United States Patent
Taguchi

[19]

[11] Patent Number: 5,825,842
[45] Date of Patent: Oct. 20, 1998

[54] X-RAY COMPUTED TOMOGRAPHIC IMAGING DEVICE AND X-RAY COMPUTED TOMOGRAPHIC METHOD

[75] Inventor: Katsuyuki Taguchi, Otawara, Japan

[73] Assignee: Kabushiki Kaisha Toshiba, Kawasaki, Japan

[21] Appl. No.: 675,832

[22] Filed: Jul. 5, 1996

[30] Foreign Application Priority Data

Jul. 5, 1995 [JP] Japan .................................. 7-169963

[51] Int. Cl.$^6$ ....................................................... A61B 6/03
[52] U.S. Cl. ............................................ 378/15; 378/901
[58] Field of Search ............................... 378/4, 15, 901

[56] References Cited

U.S. PATENT DOCUMENTS

| | | | |
|---|---|---|---|
| 4,965,726 | 10/1990 | Heuscher et al. ........................... | 378/19 |
| 5,291,402 | 3/1994 | Pfoh ........................................... | 378/13 |
| 5,377,250 | 12/1994 | Hu .............................................. | 378/15 |
| 5,430,783 | 7/1995 | Hu et al. .................................... | 378/15 |
| 5,541,971 | 7/1996 | Saito .......................................... | 378/15 |
| 5,583,903 | 12/1996 | Saito et al. ................................. | 379/19 |

FOREIGN PATENT DOCUMENTS

| | | |
|---|---|---|
| 4-224736 | 8/1992 | Japan . |
| 7-194590 | 8/1995 | Japan . |

OTHER PUBLICATIONS

Journal of the Japanese Institute of Electronic Information Communication, DII vol. J 74–D–II, No. 8, pp. 1108–1114, Aug. 1991, Hiroyuki Kudo, et al., "Three–Dimensional Helical–Scan Computed Tomography Using Cone–Beam Projections".

*Primary Examiner*—David P. Porta
*Assistant Examiner*—David Vernon Bruce
*Attorney, Agent, or Firm*—Oblon, Spivak, McClelland, Maier & Neustadt, P.C.

[57] ABSTRACT

An x-ray computed tomography system and method having a reconstruction processing circuit that interpolates projection data for an x-ray beam path from 2N detector elements in a detector array proximate to a point where the x-ray beam path intersects the detector array. The system and method can also extrapolate data from 2N detector elements when the x-ray path intersects the detector array in an uppermost or lowermost detector row. The system and method determines an overlap region between two x-ray beams and can perform backprojection in the overlap region based upon both of the overlapping beams. The system can also determine a border region in the overlap region and perform backprojection in the border region based upon the two overlapping beams and in the remainder of the overlap area based upon cone angles of the x-ray beams. The system can also cancel or attenuate image artifacts by varying the helical scanning pitch, and can apply position-dependent and/or angular-dependent weighting.

83 Claims, 21 Drawing Sheets

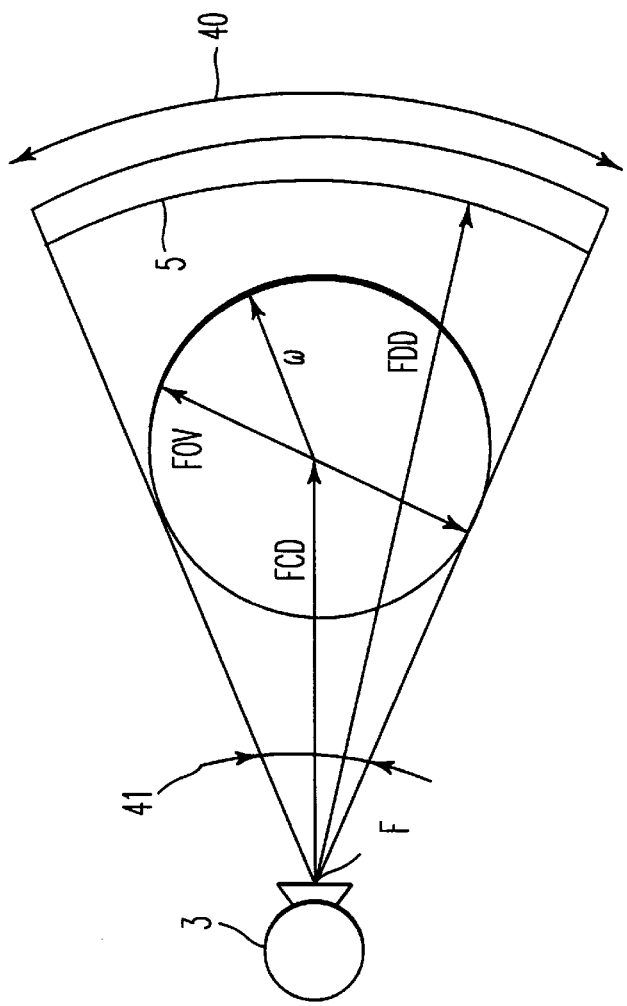
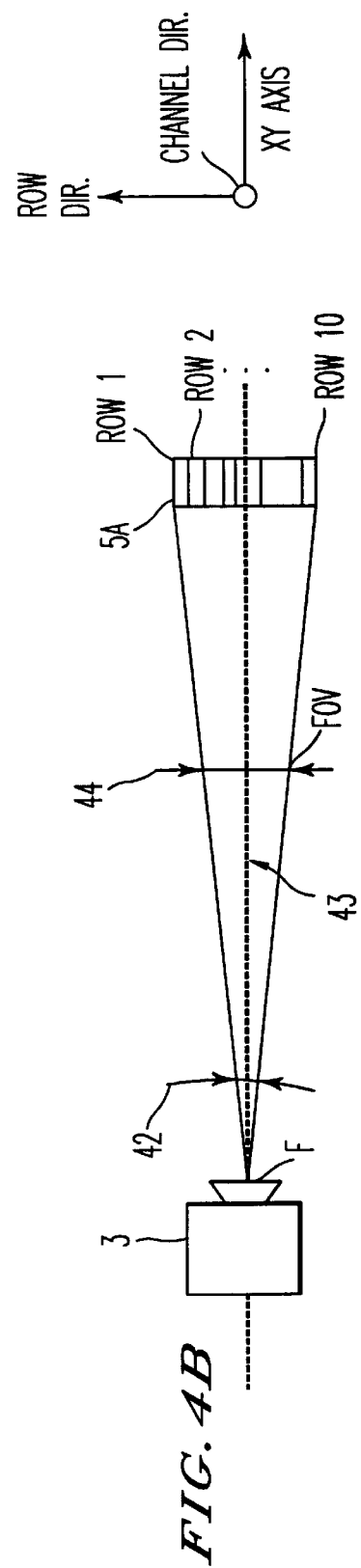
FIG. 4A
FIG. 4B

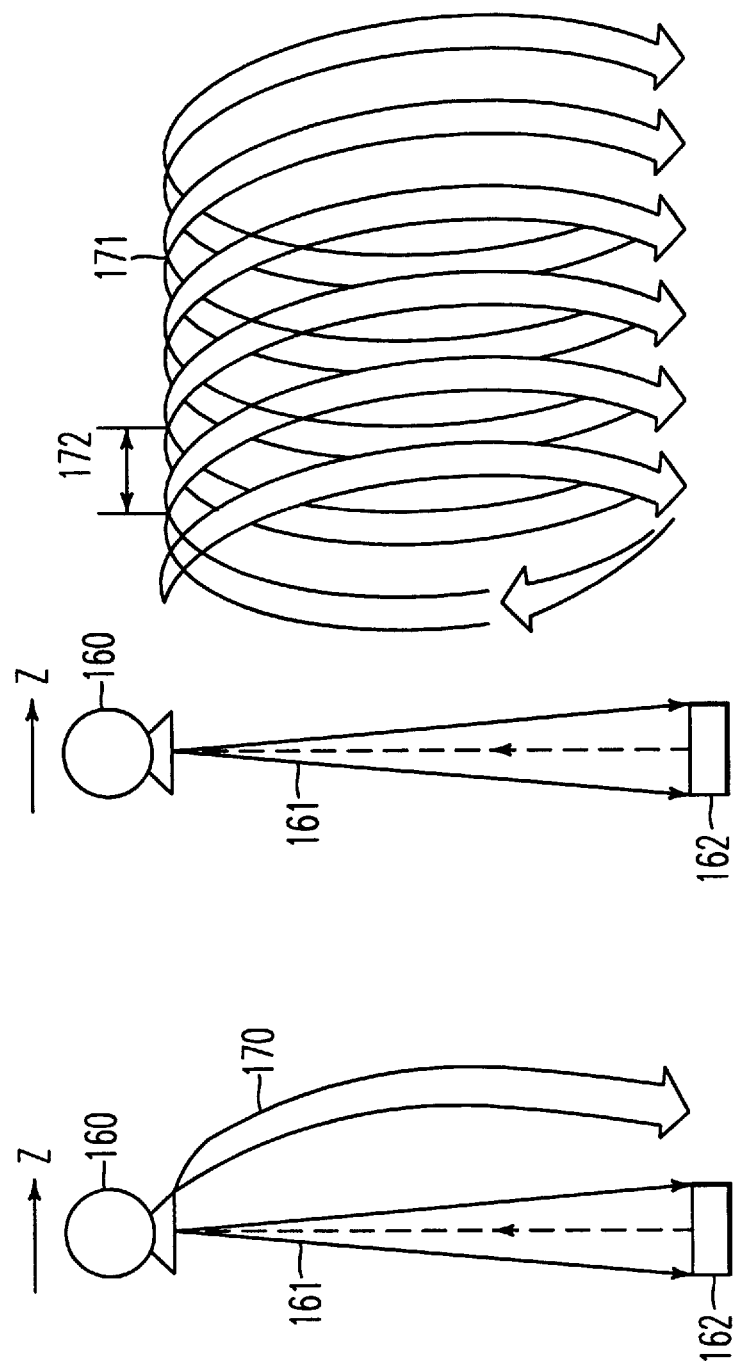

X-RAY COMPUTED TOMOGRAPHIC IMAGING DEVICE AND X-RAY COMPUTED TOMOGRAPHIC METHOD

BACKGROUND OF THE INVENTION

1. Field of the Invention

The present invention relates to an x-ray computed tomographic imaging device and an x-ray computed tomographic method, and more particularly to a device and method in which a subject is helically scanned by a cone-beam of x-rays.

2. Discussion of the Background

Third-generation CT is defined as a system in which, as shown in FIG. 16, an x-ray tube 160 that generates an x-ray flux 161 and an x-ray detector 162 having detector elements 163 (for example, 1000) arranged facing the tube on the opposite side of the subject are rotated about the subject while projection data is collected from various angles. The x-ray flux 161 completely covers the field of view (FOV) or slice of the subject 164. Conventionally, the x-ray flux 161 consisted of a fan-shaped beam of x-rays, and the detector 162 was a one-dimensional array-type x-ray detector.

Two types of scanning systems are employed: conventional scanning and helical scanning. As shown in FIG. 17(a), conventional scanning is defined as a scanning system in which the x-ray tube 160 is moved around the periphery of the same circular track indicated by arrow 170. As shown in FIG. 17(b), a helical scanning system is defined as a scanning system wherein the x-ray source 160 and the detector 162 rotate continuously about the subject and the bed on which the subject is placed is moved along the body axis synchronously with this revolution; this term is employed because, considering a moving co-ordinate system that moves with the subject, the x-ray tube describes a helical orbit 171. In the moving co-ordinate system, the distance in the body-axis (or z-axis) direction through which the x-ray tube is displaced in one rotation is defined as the helical pitch, indicated as 172.

In recent years CTs, known as third generation or fourth generation CTs, have an x-ray tube that generates a cone-beam of x-ray flux that widens out in the direction of the body axis, rather that a fan-shaped beam of x-ray flux, and a two-dimensional array-type x-ray detector wherein the detector elements are arranged in matrix fashion. The x-ray detector has a plurality of one-dimensional array-type detectors are stacked in a plurality of rows, for example N rows, in the z-axis direction. This is called cone-beam CT.

At this point, consider an x-ray beam incident on detectors constituting a single row as shown in FIGS. 18 and 19. X-rays from focal spot 180 are emitted in a cone beam 182 through a collimator 185 onto detector array 183 having detector rows D1–DN. The thickness in the direction of the z-axis when this x-ray beam passes through the center of revolution 181 (center of the z-axis i.e. imaging region field of view) is defined as the basic slice thickness 184 of a cone-beam CT. Also, the imaging region in a third generation cone-beam CT is defined as a cylinder of radius omega centered on the z-axis. Several image reconstruction methods in the case of scanning with a conventional cone-beam CT are know, for example, as described below.

In "Practical Cone-Beam Algorithm" by Feldkamp et al, J. Opt. Soc. Am. A, vol. 1, no. 6, pp. 612–619 (June 1984), a method of reconstruction is described, termed the Feldkamp reconstruction method from the name of its developer. It is an approximate three-dimensional reconstruction algorithm obtained by expanding the fan beam (in a two-dimensional plane) reconstruction algorithm (which is a mathematically straight reconstruction method) in the z-axis direction. It comprises the following steps:

(1) Correction and weighting of projection data: The beam-spreading effect is corrected by multiplying the projection data by weights corresponding to the z-coordinate.

(2) Convolution: The data of (1) are convolved with a reconstruction function which is the same as in fan-beam reconstruction.

(3) backprojection: The data of (2) are added at points (voxels) on the path that the x-rays pass through (from the focal point to the detector).

Image reconstruction is achieved by repeating the above steps (1) to (3) over prescribed angles (360° or 180° + fan angle). In all of the above, the results of computer simulation are given after the mathematical processing. This method of reconstruction is basically an approximate method, so the image quality of the reconstructed image deteriorates as the spread of the beam in the z-axis direction increases, i.e. as the cone angle increases. This imposes limitations on the cone angle that is practicable in medical equipment, etc. Also, various methods of reconstruction involving partial modification of the above by, for example, altering the direction of the convolution processing have been reported, and, regarding Feldkamp reconstruction, many experiments have been reported involving the use of computer simulation and/or imaging plates etc.

In this specification, however, "Feldkamp reconstruction" will be used as a general term encompassing processing involving image reconstruction taking into account the spread of the beam in the z-axis direction by for example backprojection calculation on the path passed through by the x-ray.

In recent years, consideration has been given to combining cone beam CT with the helical scan system in order to achieve collection of three-dimensional data relating to an imaging region FOV that is comparatively broad in the z-axis direction with high resolution and yet high speed. Such a combined system is described in "CT Device" by Hiroshi Aratade and Kyojiro Nambu (Early Japanese Patent Publication No. H.4-224736, applied for on 25 Dec. 1990), and in "Three-dimensional Helical Scan CT Using cone-beam Projection" by Hiroyuki Kudo and Tsuneo Saito (Journal of the Japanese Institute of Electronic Information Communication, DII Volume J 74-D-II, No. 8, pp 1108–1114, August 1991).

These references disclose a method of reconstruction that is similar to the Feldkamp reconstruction. Briefly, as in the case of the Feldkamp reconstruction described above, this method consists in weighting the projection data, convolving with a function, and weighted backprojection on to the x-ray path over 360°. Considering this backprojection at a particular reconstruction point (voxel), the data obtained through the path connection the focal point and the reconstruction point in each view are weighted at the reconstruction point and data of x-ray paths corresponding to the number of views obtained over 360° are added. Reconstruction of the point in question is thereby achieved.

Regarding the helical pitch, as shown in FIG. 20, the Kudo et al reference states "it is a necessary and sufficient condition that the point of intersection 200 of the top edge 201 of the x-ray beam emitted from position 202 of the x-ray source and the bottom edge 203 of the x-ray beam emitted from position 204 (B+2v) of the x-ray source after one revolution is positioned outside of the region where the body

205 being irradiated by the x-ray source is positioned. This can also easily be inferred from the fact that x-ray beams over a sufficient angle, e.g. 360°, are required at the reconstruction points needed to perform the aforementioned image reconstruction.

In the Aratade et al and Kudo et al references, there is no discussion of the effect of divergence of the x-ray beam, i.e. no discussion of the fact that the channels of the detectors are restricted in the channel direction and z-axis direction and have a certain size. Also, although the results of computer simulations are given, the details of these, for example, the method of interpolation, are not given.

These two references are subject to a number of problems. First, there is a reconstruction error due to the fact that the detector element of a single channel has a certain size in the z-axis direction and channel direction. To begin, the two references simply consist of a purely mathematical treatment followed abruptly by the results of computer simulations. In the reconstruction processing, the cylindrical imaging region FOV is defined as an assembly of a plurality of voxels. Since on the computer it is possible to generate at will data at the point on the detector plane intersected by the straight line from the focal point to the voxel which it is desired to reconstruct, the effect of any divergence between these lines does not appear in the results. Also, with a detector such as an I.I. (image intensifier) that is employed in several of the experiments, the detector elements are formed in square shape 0.5 mm square or less; this size is practically negligible and the vertical and horizontal sizes are equal.

In contrast, in an actual cone-beam CT or the like, the sizes of the detector elements in the channel direction and the z-axis direction are respectively about 1 mm×2 mm. Since the x-ray path of the measured projection data is identified as the straight line joining the x-ray focal point and the center of the channel, in many cases, this measured x-ray path deviates from the calculated x-ray path joining the x-ray focal point and the center of the voxel defined for reconstruction processing. This deviation gives rise to error. Although, in a case where an I.I. is used, if the size of the detector elements is sufficiently small so that they can be treated as points, this deviation can be neglected and the data of the measured x-ray path at the position closest to the calculated x-ray path can be employed in practice. If, as in the case of the detector in a cone beam CT, the detector element size is large, this error cannot be neglected. When the size of the detector element in the z-axis direction is even larger, this error becomes even greater.

Another problem relates to the treatment of data in overlapping regions. As described in Kudo et al, if the helical pitch is determined, as shown by the shaded region 210 in FIG. 21(a), the x-ray beam from the focal spot in the kth rotation 211 and x-ray beam from the focal spot in the (k+1)th rotation 212 overlap. This means that the information of the shaded, overlapping region 210 is contained in two sets of projection data. However, in Kudo et al this overlapping region is neglected, and backprojection is performed using only x-ray beams of small angle of intersection, i.e. the cone angle with respect to the reconstruction plane that is sought to be obtained. Thus the information in region 210 is insufficiently utilized.

Another problem relates to the generation of a streak in the direction of the joint of the angle of commencement of reconstruction and the angle of termination of reconstruction. FIG. 21(b) shows the outline of the cone angle from the focal point of the x-rays with respect to the center of revolution of the reconstruction plane when reconstruction is performed, as in Kudo et al, using projection data for which the cone angle of the reconstruction plane in question is made as small as possible. The reconstruction commencement angle and reconstruction termination angle are adjacent, but, whereas the cone angle at the reconstruction commencement angle is +10°, and the cone angle in the case of the reconstruction termination angle is −10°,it can be seen that there is a large gap due to discontinuity of this cone angle in the direction (broken line 220) of this joint. Also, there is the effect of movement of the subject owing to the fact that the data are collected at different times, giving rise to a clearly apparent streak artifact in this direction.

Lastly, there is a problem in that the helical pitch is small. It is stated in Kudo et al that "it is necessary and sufficient that the point of intersection of the upper edge and lower edge of the x-ray beam is positioned outside the region where the subject is located", but there is no description regarding channel size of the detector or of the divergence. In other words, this may be interpreted as (See FIG. 22) "it is necessary and sufficient that the point of intersection [220] of the x-ray path [221] passing through the center of the channel [223] of the topmost row of the detector and the x-ray path [222] passing through the center of the channel [224] of the bottom-most row should be positioned outside the region where the subject is located" (the region border is indicated as 226) and means that the helical pitch 225 becomes quite small. The x-rays emitted at the kth and (k+1)th revolutions are indicated as 227 and 228, respectively. For example, if the number of rows of the detector is N, the basic slice thickness is "Thick", the focal point to center of revolution distance is FCD, and the effective diameter of the field of vision is FOV, the helical pitch P is defined by:

$$P \leq \text{Thick} \times (N/2 - 0.5) \times (FCD - FOV/2)/FCD \times 2.0 \quad (1)$$

If for example N=10, Thick=2 mm, FCD=500 mm, and FOV=240 mm, P=13.68 mm/rev. This is fairly small, making the scanning time very long.

SUMMARY OF THE INVENTION

An object of the present invention is to provide an x-ray computed tomographic imaging device and method in which image quality is improved by reducing the error in reconstruction resulting from displacement of the measured x-ray path from the calculated x-ray path.

Another object of the present invention is to provide an x-ray computed tomographic imaging device and method wherein the projection data of the overlapping region of the kth revolution of the x-ray beam and of the (k+1)th revolution of the x-ray beam are handled in a way leading to improved image quality.

A further object of this invention is to provide an x-ray computed tomographic imaging device and method wherein the occurrence of the streak artifact produced by discontinuity of the cone angle is mitigated.

These and other objects of the invention are achieved by an x-ray computed tomographic imaging device where, while moving an x-ray tube that directs a cone-beam of x-rays onto a subject relatively along a helical orbit as seen from the subject, the x-rays passing through the subject are detected by a 2-dimensional array-type x-ray detector, wherein a plurality of detector elements are arranged in 2-dimensional fashion, and backprojection data are obtained reflecting respective x-ray absorption coefficients for a plurality of voxels defined in the imaging region, by backprojection of the projection data that are obtained. The backprojection data of a specified voxel is found based on a plurality of projection data measured around the point of intersection of the detector surface of the 2-dimensional array-type x-ray detector and the calculated x-ray path joining the center of the specified voxel and the x-ray focal spot. The displacement between the measured projection data x-ray path and the calculated x-ray path is reduced, thereby raising image quality.

These and other objects are also achieved by an x-ray computed tomographic imaging device where the backprojection data of a specified voxel within the region of overlap of the cone-beam x-ray flux from the x-ray tube on the kth revolution with the cone-beam x-ray flux from the x-ray tube on the (k+1)th revolution are found using the projection data along the x-ray path through the specified voxel collected on the kth revolution and the projection data along the x-ray path through the specified voxel collected on the (k+1)th revolution. Since the backprojection data of specified voxels in the overlapping region is found using projection data collected on the kth revolution and using projection data collected on the (k+1)th revolution, image quality is improved compared with the convention device where the overlapping region is found using only one of these data.

Also, in an x-ray computed tomographic imaging device according to the invention, while moving an x-ray tube that directs a cone-beam of x-rays onto a subject relatively along a helical track as seen from the subject, the x-rays passing through the subject are detected by a 2-dimensional array-type x-ray detector and backprojection data are obtained reflecting respective x-ray absorption coefficients for a plurality of voxels defined in a cylindrical imaging region centered on the center line of the helical track by backprojection of the projection data that are obtained. The interval of the helical orbit may be set to a non-integral multiple of the basic slice thickness.

When the pitch of the helical orbit is set to a non-integral multiple of the basic slice thickness, the position of changeover between the kth revolution projection data and the (k+1)th revolution projection data does not occur in the same position on successive scans, reducing the occurrence of the streak artifact produced by the discontinuity of the cone angle.

BRIEF DESCRIPTION OF THE DRAWINGS

Many of the attendant advantages are apparent from the following detailed description taken in conjunction with the following drawings, wherein:

FIGS. 4(a) and 4(b) are diagrams illustrating various parameters of the device;

FIGS. 12(a), 12(b) and 12(c) are diagrams illustrating the shape of a border area, a top view of a reconstruction plane, and another border area within the overlapping region, respectively;

FIGS. 17(a) and 17(b) are diagram illustrating conventional scanning and helical scanning;

DETAILED DESCRIPTION OF THE PREFERRED EMBODIMENTS

Figure 1:
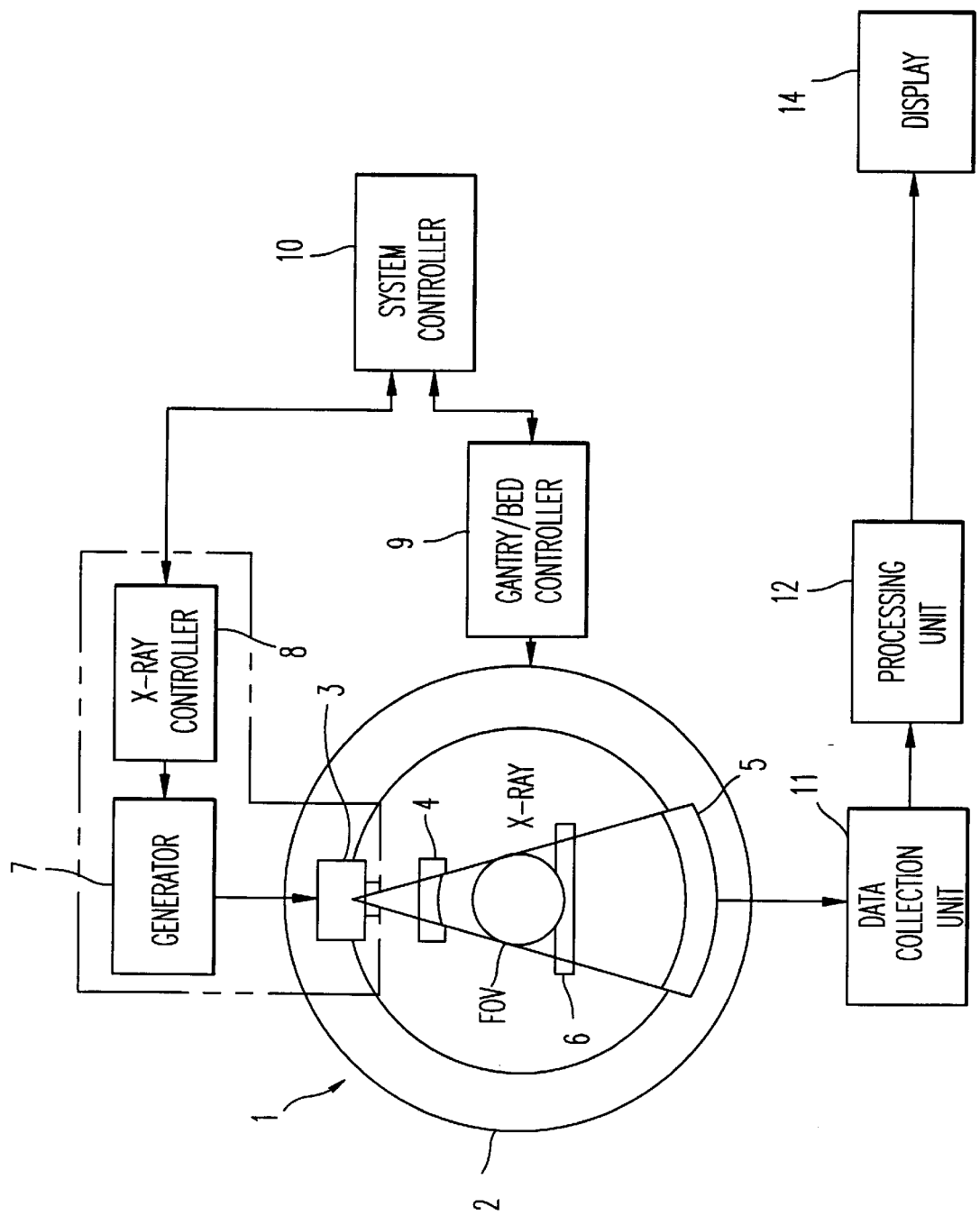
FIG. 1 is diagram of an x-ray computed tomographic imaging device according to a first embodiment of the invention.
Figure 2:
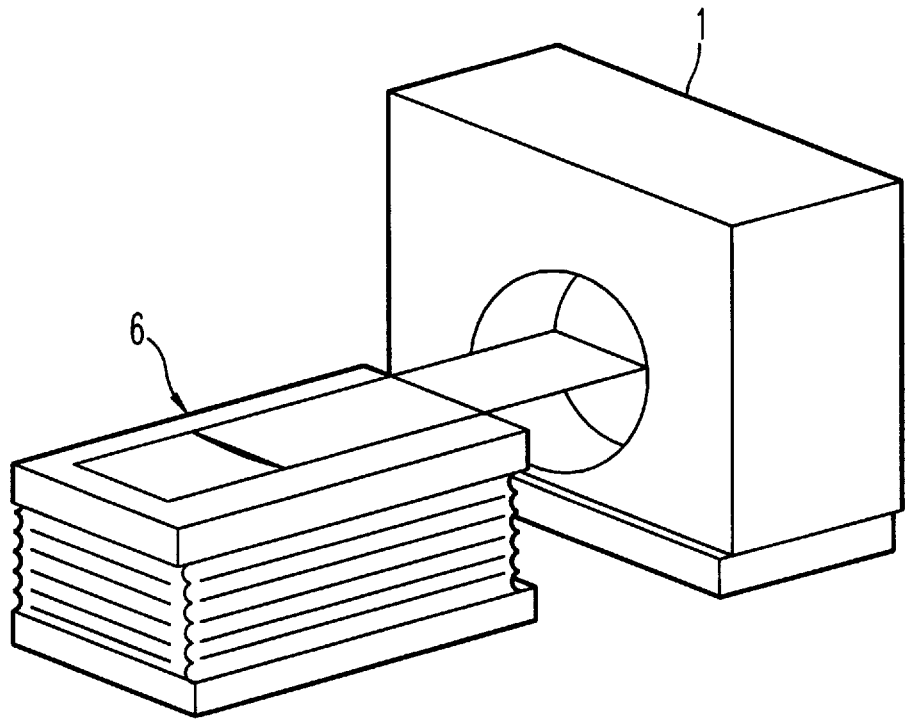
FIG. 2 is a perspective view of a gantry of FIG. 1.
Figure 3:
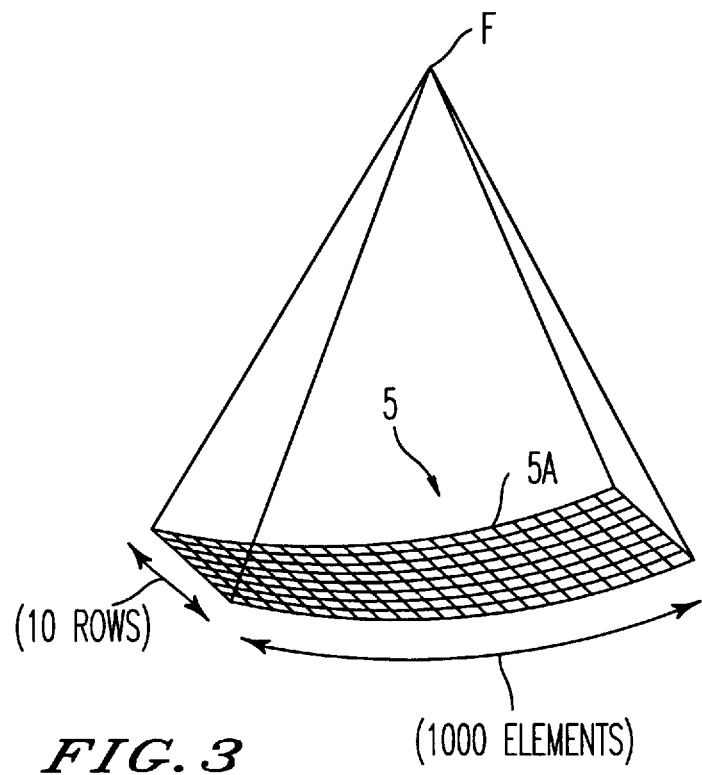
FIG. 3 is a perspective view of a two-dimensional array type x-ray detector of FIG. 1.

The preferred embodiments of the present invention will be described below with reference to the drawings, in particular FIG. 1 which shows an x-ray computed topographic imaging device according to a first embodiment of this invention. FIG. 2 is a perspective view of the gantry of FIG. 1 and FIG. 3 is a perspective view of a two-dimensional array type detector of FIG. 1. The projection data measurement system constituted by gantry 1 accommodates an x-ray source 3 that generates a cone-beam of x-ray flux approximately cone-shaped, and a two-dimensional array type x-ray detector 5 consisting of a plurality of detector elements 5A arranged in two-dimensional fashion, i.e., a plurality of elements arranged in one dimension stacked in a plurality of rows. In FIG. 3, ten rows each having 1000 elements are shown (other arrangements are possible), with the x-ray flux shown schematically emitted from focal point F.

X-ray source 3 and two-dimensional array type x-ray detector 5 are installed on a rotating ring 2 in facing opposite sides of a subject, who is laid on a sliding sheet of a bed 6. Two-dimensional array type x-ray detector 5 is mounted on rotating ring 2. Each detector element will correspond with one channel. X-rays from x-ray source 3 are directed on to subject through an x-ray filter 4. X-rays that have passed through the subject are detected as an electrical signal by two-dimensional array type x-ray detector 5.

X-ray controller 8 supplies a trigger signal to high voltage generator 7. High voltage generator 7 applies high voltage to x-ray source 3 with the timing with which the trigger signal is received. This causes x-rays to be emitted from x-ray source 3. Gantry/bed controller 9 synchronously controls the revolution of rotating ring 2 of gantry 1 and the sliding of the sliding sheet of bed 6. System controller 10 constitutes the control center of the entire system and controls x-ray controller 8 and gantry/bed controller 9 such that, as seen from the subject, x-ray source 3 executes so-called helical scanning, in which it moves along a helical path. Specifically, rotating ring 2 is continuously rotated with fixed angular speed while the sliding plate is displaced with fixed speed, and x-rays are emitted continuously or intermittently at fixed angular intervals from x-ray source 3.

The output signal of two-dimensional array type x-ray detector 5 is amplified by a data collection unit 11 for each channel and converted to a digital signal, to produce projection data. The projection data that is output from data collection unit 11 is fed to reconstruction processing unit 12. Reconstruction processing unit 12 uses the projection data to find backprojection data reflecting the x-ray absorption in each voxel. In the helical scanning system using a cone-beam of x-rays as in the first embodiment, the imaging region (effective field of view) is of cylindrical shape of radius ω centered on the axis of revolution. Reconstruction processing unit 12 defines a plurality of voxels (three-dimensional pixels) in this imaging region, and finds the backprojection data for each voxel. The three-dimensional image data or tomographic image data compiled by using this backprojection data is sent to display device 14, where it is displayed visually as a three-dimensional image or tomographic image.

Figure 5A:
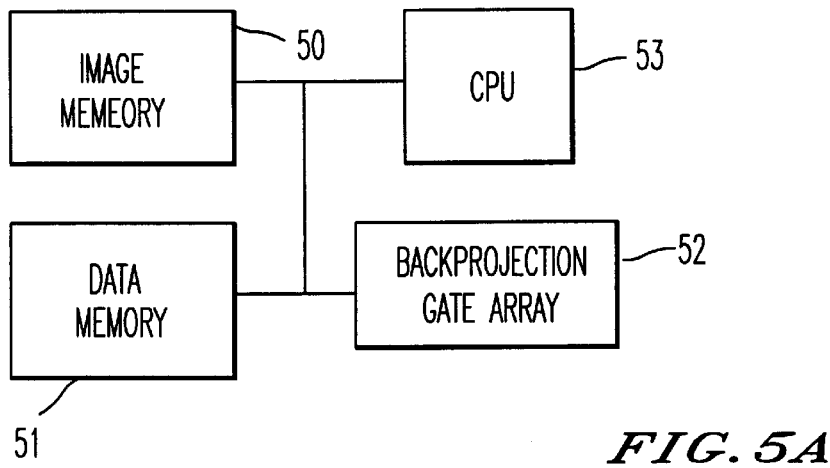
FIGS. 5(a) and 5(b) are diagrams of the reconstruction processor and circuits included therein according to the invention.

A diagram of the reconstruction processor 12 is shown in FIG 5(*a*). Projection data from circuit 11 are stored in data memory 51. An image memory 50 is provided for storage of reconstructed image data or storage of image data which are being reconstructed. Memories 50 and 51 can be implemented as RAM or other semiconductor memory. Backprojection gate array 52 consists of an interpolation circuit, a weighting circuit and a backprojection circuit, and carries out interpolation, weighting and backprojection operations. Circuits 50–52 and their operations are controlled by CPU 53. CPU 53 can determine an overlap area of x-ray beams, perform the operations of the weighting circuit included in the gate array 52, and carry out desired processing on the projection data such a convolution. A separate convolution circuit may be provided in the circuit of FIG. 5(*a*). In the following description projection data refers to data both before and after processing such as convolution.

A more detailed diagram of another construction of the reconstruction processor 12 is shown in FIG. 5(*b*). Image memory 50 and data memory 51 are connected to CPU 53. Also connected to, and controlled by CPU 53 are an interpolation circuit 54, an extrapolation circuit 55 and a weighting circuit 56. A convolution circuit 57 performs convolution or other required processing on the projection data and backprojection circuit 58 performs backprojecting. The processors 12 shown in FIGS. 5(*a*) and 5(*b*) could be implemented in hardware, such as a programmed microcomputer, or could be implemented as software. For example gate array 52 could be implemented as a semiconductor gate array.

Figure 18:
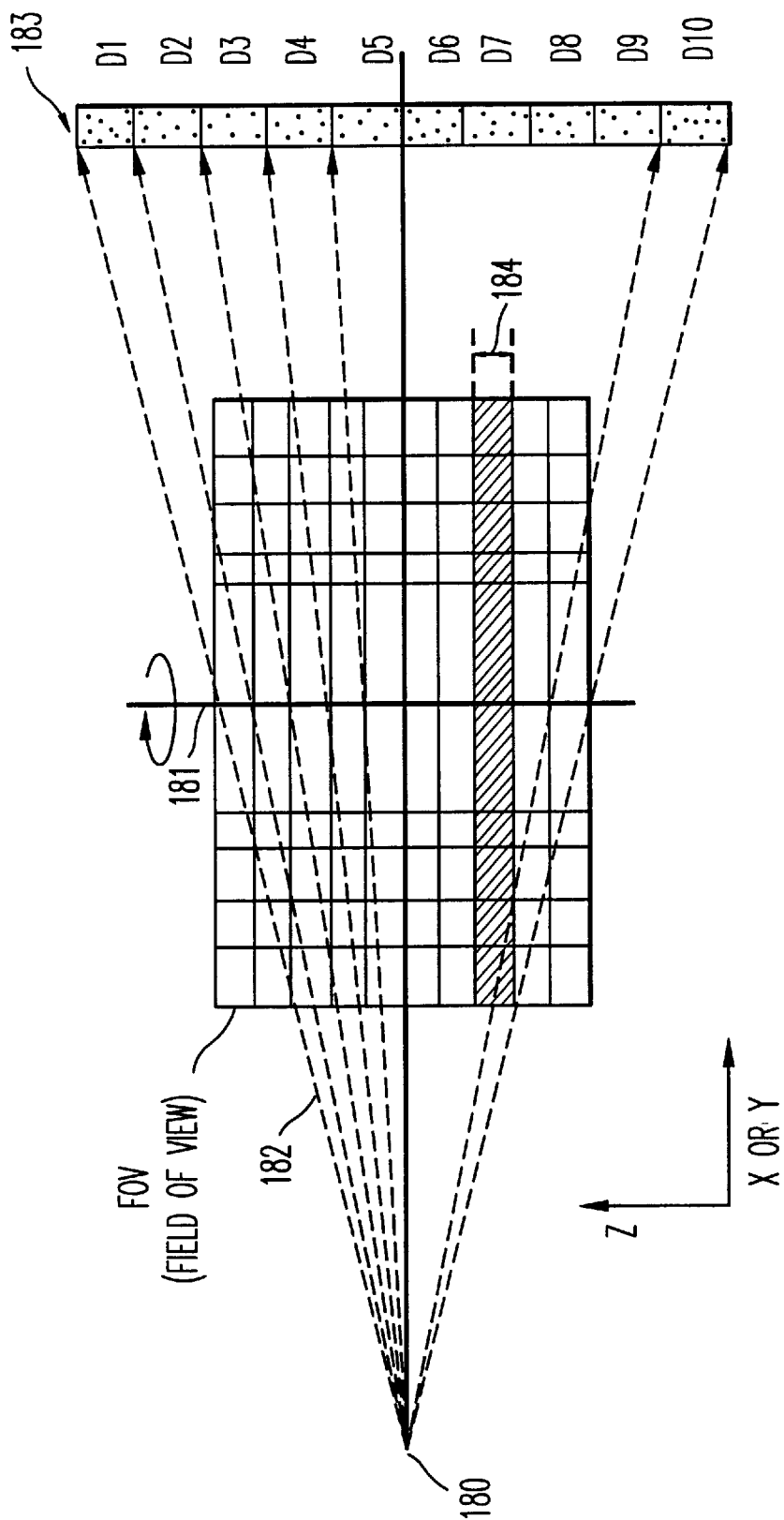
FIG. 18 is a diagram illustrating slice thickness.
Figure 19:
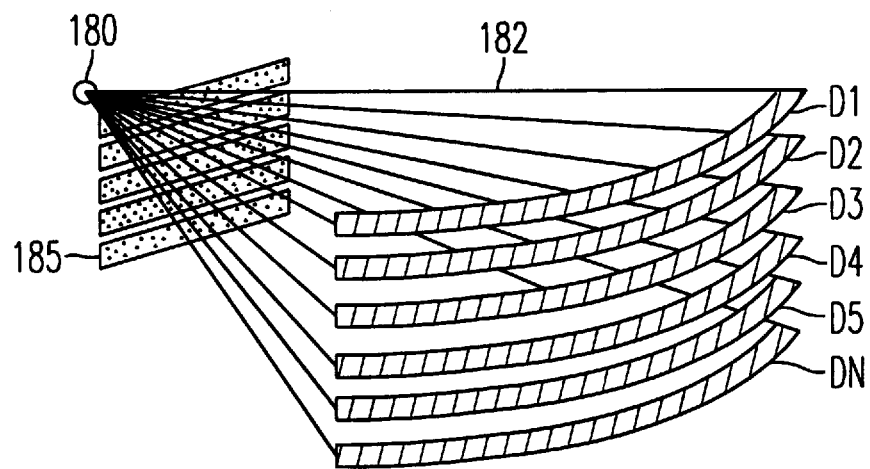
FIG. 19 is a diagram illustrating conventional cone-beam scanning.
Figure 20:
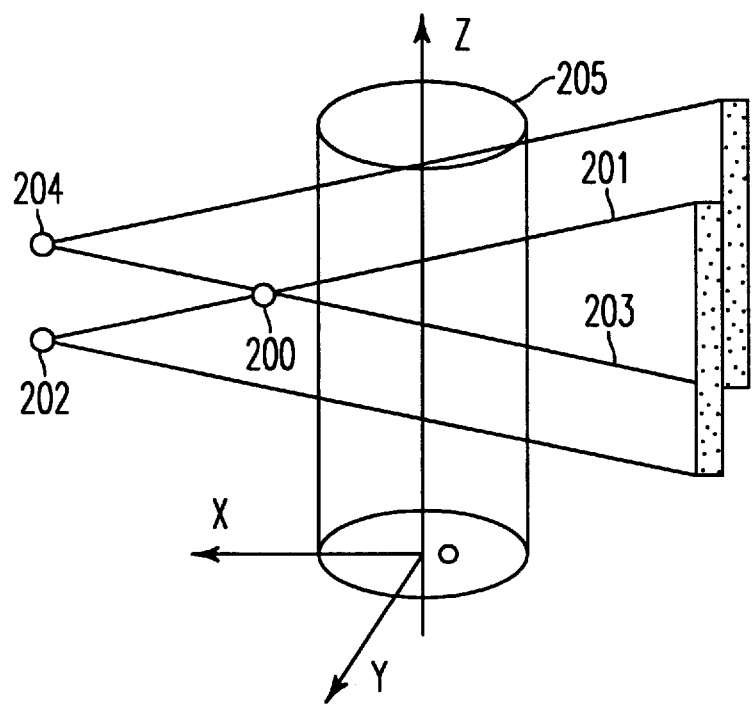
FIG. 20 is a diagram illustrating the conventional restriction of the helical pitch.
Figure 21A:
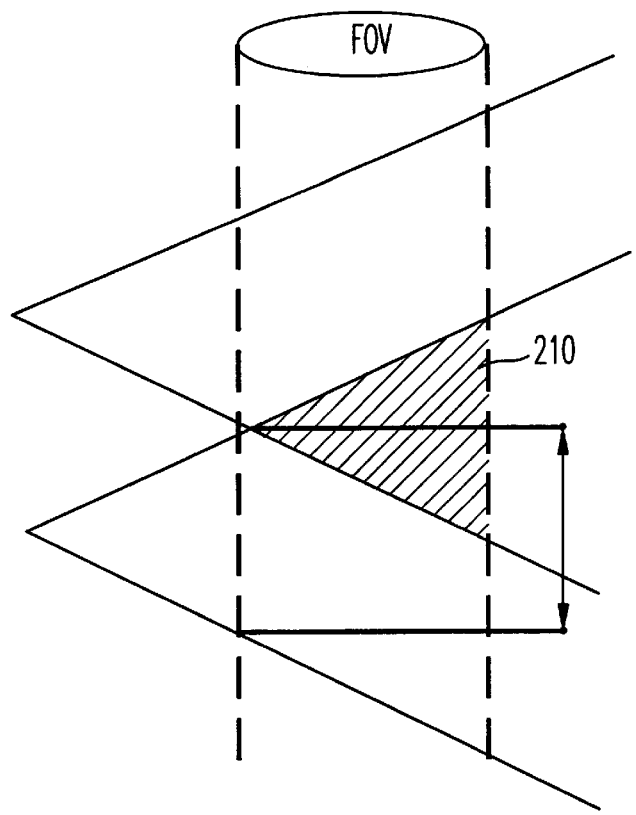
FIGS. 21(a) and 21(b) are diagrams illustrating an overlapping region and a cone angle, respectively.
Figure 21B:
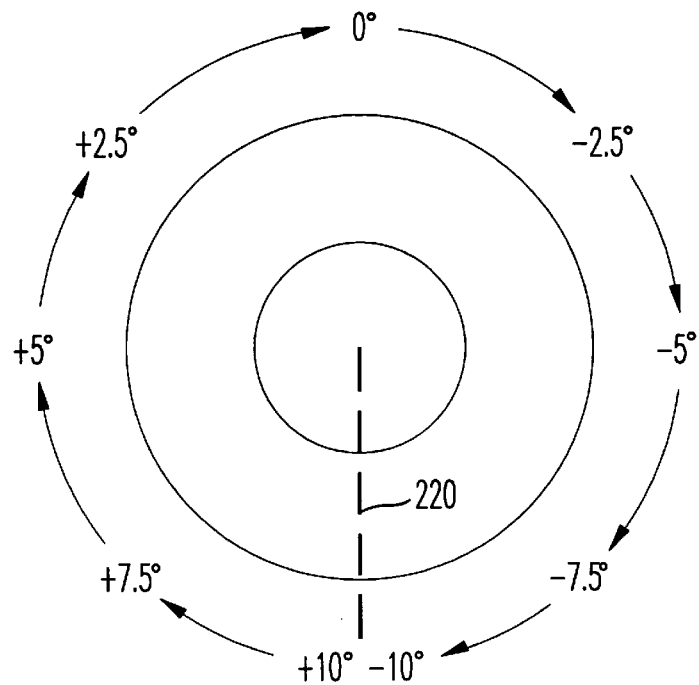
Figure 21C:
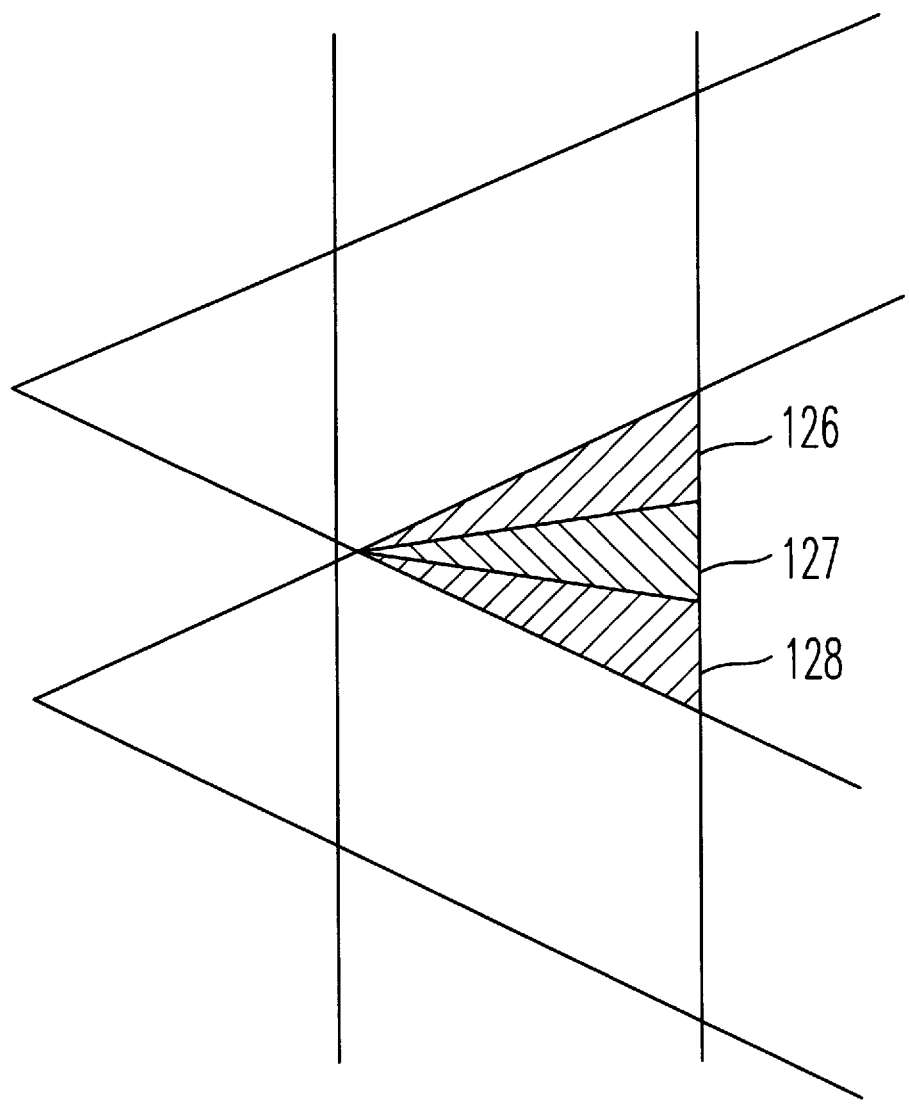

Next, the operation of this system, including the reconstruction processors 12 as shown in FIGS. 5(*a*) and 5(*b*), will be described. For the system geometry, as one example, N=10, Thick=2mm, FCD=500 mm, and FOV=240 mm will be selected. As shown in FIG. 4(*a*) and FIG. 4(*b*), N is the number of detector rows, Thick is the thickness of the basic slice, FCD is the focal point–center of revolution distance, ω is the diameter of the imaging region FOV (effective field of view), and P is the helical pitch. Also shown in FIG. 4(*a*) is the fan angle 41, the channel direction 40 and the focal point to detector array distance FDD. The basic slice thickness is defined as the thickness of the x-ray beam incident on a detector element 5A corresponding to one channel in the vicinity of the imaging region FOV, as described in FIG. 18. The helical pitch P is defined as the separation of the helical track of x-ray source 3 (see reference numeral 172 in FIG. 17(*b*); specifically, it is defined as the distance moved by the sliding sheet while x-ray source 3 performs one revolution.

In FIG. 4(*b*), x-ray source 3 emits a beam of x-rays having a cone angle 42 and a central plane 43. The total basic slice thickness is illustrated as 44. The x-ray beam passes through the imaging region FOV and is incident upon rows 1–10 of the detector elements 5A.

The method of and system for compilation of backprojection data according to the first embodiment, will now be described. First of all, the reconstruction processing unit 12 takes into account in the calculations it performs that projection data has been obtained along the straight line (x-ray path) joining the x-ray focal point F and the center of a voxel. However, the projection data that is in fact measured is obtained along the x-ray path joining x-ray focal point F and a detector element gravity center. In the case where the input power to the detector element is uniform, the gravity center be the same as the sensitivity center. In other words, a sensitivity center will often exist on this x-ray path. On the other hand, if the detector element has a sensitivity distribution, the gravity center will not be the same as the sensitivity center. The displacement of this calculated x-ray path from the actual x-ray path constitutes a source of error that can degrade image quality.

Figure 5B:
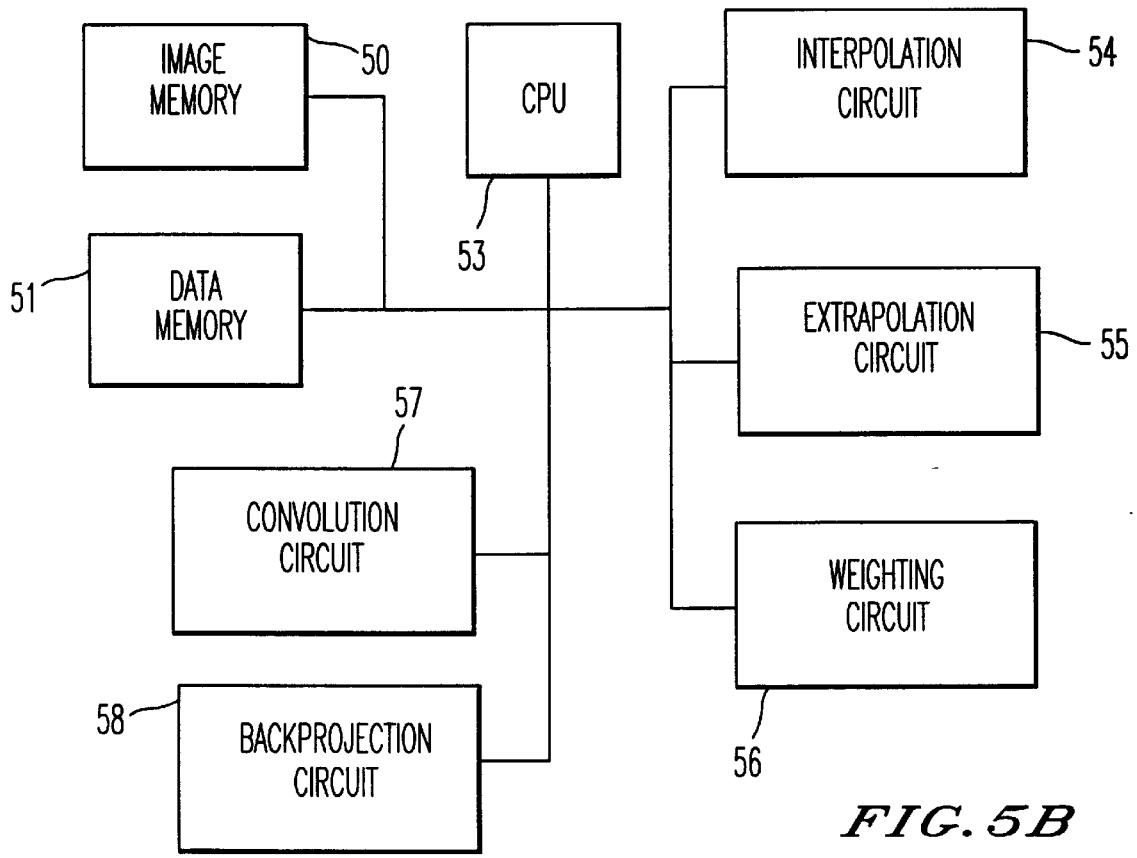
Figure 6:
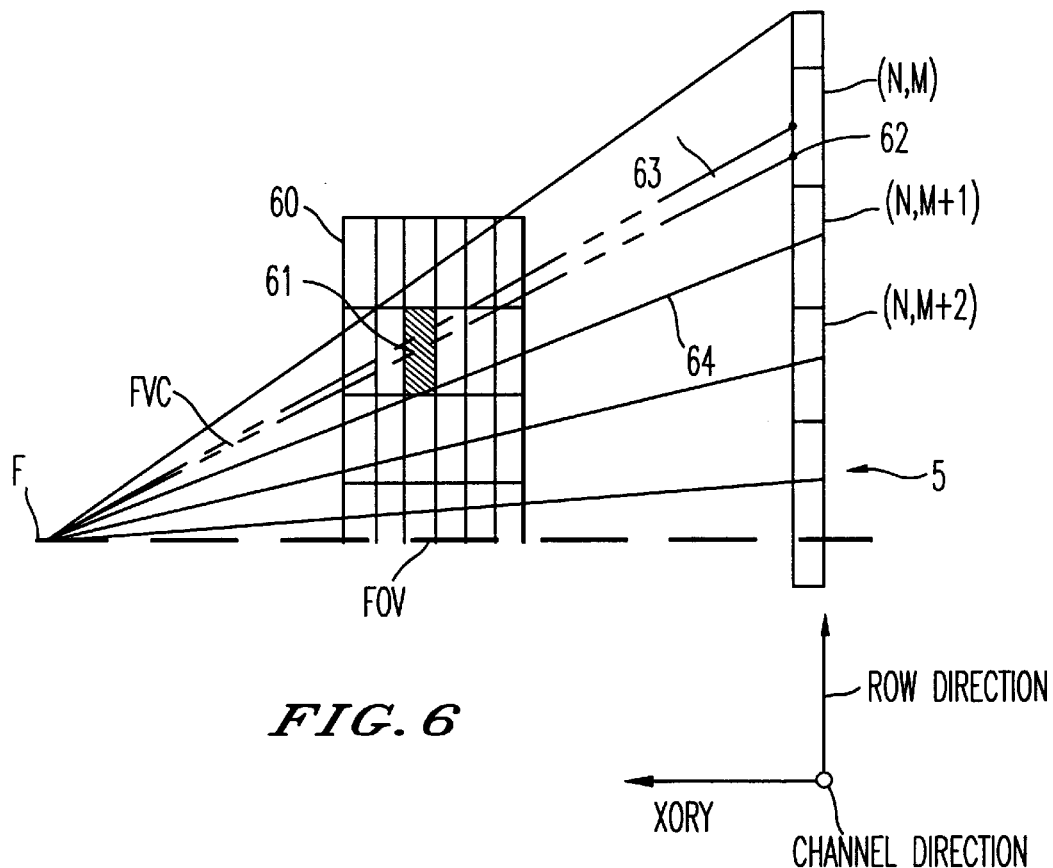
FIG. 6 is a diagram illustrating the calculation of the x-ray path.
Figure 7:
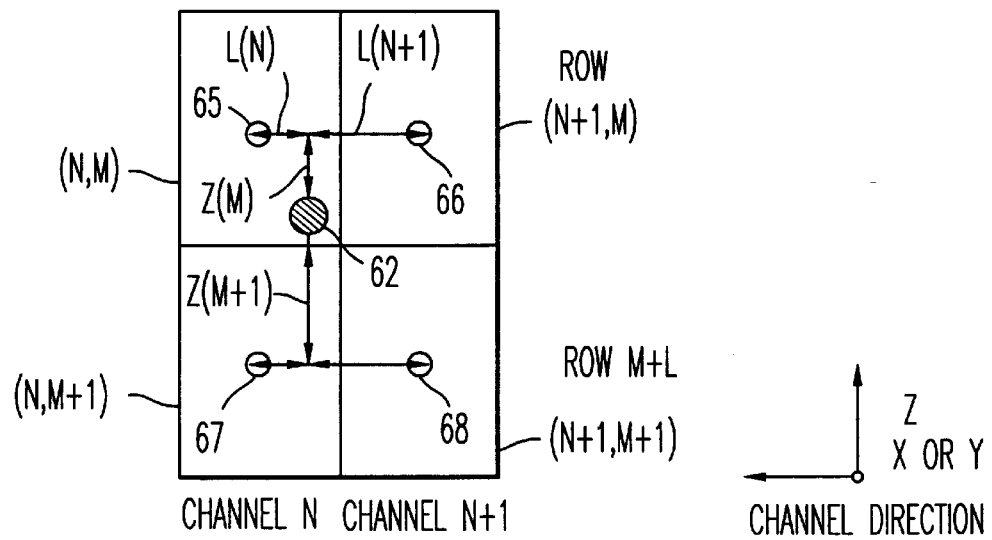
FIG. 7 is a diagram illustrating interpolation processing.

The operation of processors 12 shown in FIGS. 5(*a*) and 5(*b*) will be described with reference to FIGS. 6 and 7. FIG. 6 is a diagram showing the relationship between the x-ray beam and reconstruction voxel 60 in a particular view I (for example, at the angle of rotation of x-ray source 3 when the uppermost position is taken as 0). First, consider the backprojection of the projection data of this view in respect of voxel 61 shown by the shading. The straight line FVC joining x-ray focal point F and the center of voxel 61 is extrapolated to the point where it intersects the detector surface, taken as point 62. FIG. 7 shows the relationship between point 62 and a detector element.

Assume that point 62 is the center point of detector element (n, m), detector element (n, m+1), detector element (n+1, m) and detector element (n+1, m+1), respectively, n is the channel number and m is the row number. If the center position of each channel is defined as the center of gravity of a rectangular channel, point 62 is displaced from the center of each of the channels. If, as is often done with an I.I. detector, the data of closest detector row and channel is approximated as the data where the desired straight line FVC passes through the voxel, in the case of CT, as described above, a large error is generated. Accordingly, in the present invention, as shown by Equation (2) below, the projection data measured along the four actual x-ray paths striking points 65–68 located around the periphery of the calculated x-ray path FVC (two paths, 63 and 64, are shown in FIG. 6) is linearly interpolated by the reciprocal of the distance of point 62 from the central position of each channel, from the processed data referred to above i.e. from the data processed in respect of each of the four channels around the point 62. The interpolation is performed by backprojection gate array 52 in FIG. 5(*a*) or by interpolation circuit 54 in FIG. 5(*b*).

The interpolation data that is obtained is then used for data backprojection along straight line FVC indicating the calculated x-ray path, and weighting is applied to this backprojection.

$$Back(I) = \frac{Z(m)}{Z(m+1)+Z(m)} \left[ \frac{L(n+1)}{L(n+1)+L(n)} D(n,m+1) + \frac{L(n)}{L(n+1)+L(n)} D(n+1,m+1) \right] + \frac{Z(m+1)}{Z(m+1)+Z(m)} \left[ \frac{L(n+1)}{L(n+1)+L(n)} D(n,m) + \frac{L(n)}{L(n+1)+L(n)} D(n,m) \right] \quad (2)$$

Here, Z(m) and Z(m+1) are the distances in the z-direction from the centers of the channels in the mth and (m+1)th row to point 62, and L(n), L(n+1) are the distances on the xy plane from the centers of the channels n and n+1 to point 62.

For this embodiment, a method of linear interpolation of four data by the reciprocal of the distance has been described. However, it also possible to adopt non-linear interpolation of four data, or linear interpolation of 6, 8, . . . 2N data using data corresponding to 3, 4, . . . N rows in the z-axis direction, or nonlinear interpolation of 6, 8, . . . 2N data using data corresponding to 3, 4, . . . N rows in the z-axis direction, or to change the interpolation function in the channel direction and z axis direction. As an example, the following could be used for 3 rows where 91 is in row m, and is interpolated from rows m−1, m+1 and m+2 and channels n and n+1:

$$Back(I) = \frac{1}{3} \left[ \frac{Z(m)}{Z(m+1)+Z(m)} \left[ \frac{L(n+1)}{L(n+1)+L(n)} D(n,m+2) + \frac{L(n)}{L(n+1)+L(n)} D(n+1,m+2) \right] \right] + \frac{1}{3} \left[ \frac{Z(m+1)}{Z(m+1)+Z(m)} \left[ \frac{L(n+1)}{L(n+1)+L(n)} D(n,m-1) + \frac{L(n)}{L(n+1)+L(n)} D(n+1,m-1) \right] \right] + \frac{1}{3} \left[ \frac{L(n+1)}{L(n+1)+L(n)} (D(n,m)+D(n,m+1)) + \frac{L(n)}{L(n+1)+L(n)} (D(n+1,m)+D(n+1,m+1)) \right] \quad (3)$$

Figure 8:
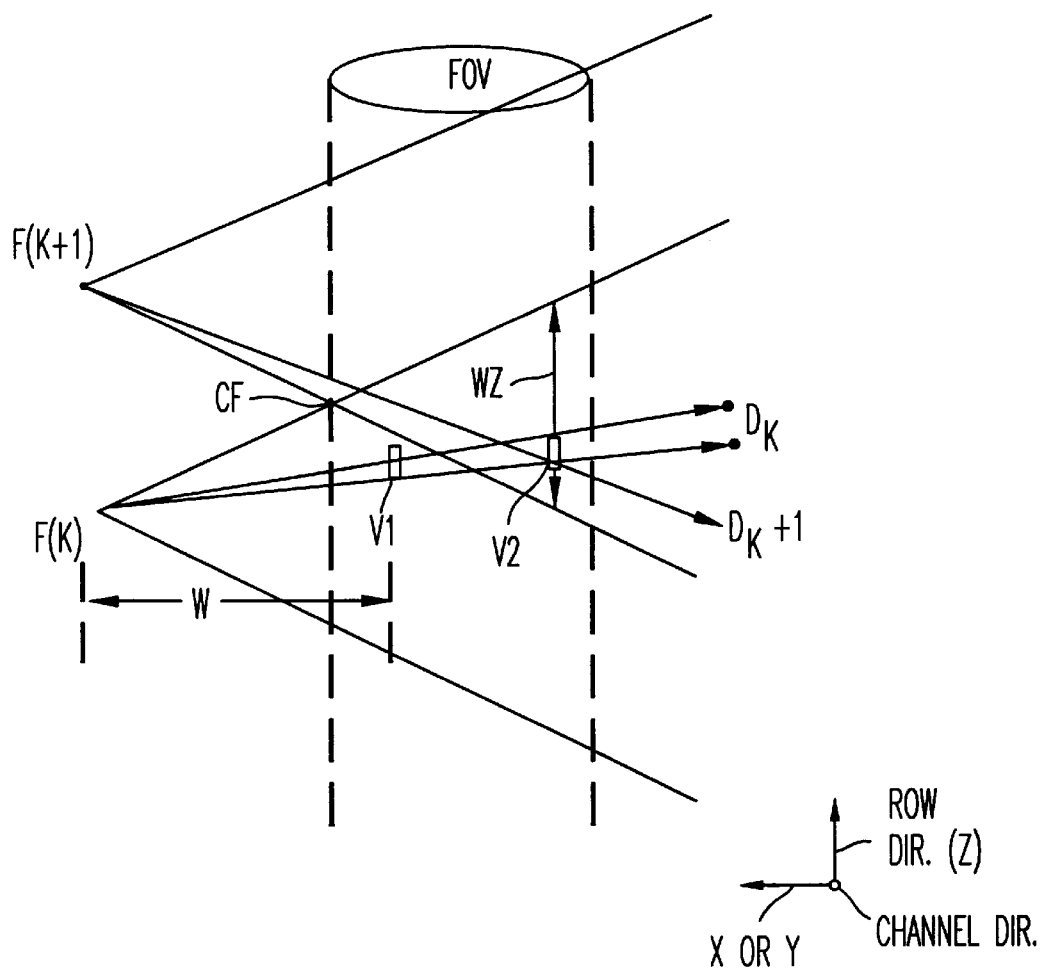
FIG. 8 is a diagram illustrating x-ray paths intersecting at voxels in an overlapping region.

A first modification of the first embodiment of the invention employing backprojection of two data in a beam overlap region, will now be described. FIG. 8 is a view, seen from the direction perpendicular to the z-axis, showing the range of incidence of the x-ray beam from x-ray focal spot F(k) on the kth revolution and the range of incidence of the x-ray beam from the x-ray focal spot F(k+1) on the (k+1)th revolution on either side of a given reconstruction plane in the same phrase. The helical scanning is executed in such a way that the range of incidence of the x-ray beam from x-ray focal spot F(k) on the kth revolution partially overlaps with the range of incidence of the x-ray beam from the x-ray focal spot F(k+1) of the (k+1)th revolution. A voxel V1 outside the overlapping region only receives the x-ray beam from focal spot F(k), so backprojection can be effected by applying weighting in accordance with Equation (4) below to the data obtained by processing the projection data obtained along the x-ray path from focal spot F(k) through voxel V1 up to the detector element:

$$Back(I,k)=1/W^2 \times D(k) \quad (4)$$

where D(k) represents the projection data subjected to prescribed processing such as convolution (by circuit 57) and W represents the distance between the two points obtained by projecting the position F of the x-ray source and the reconstruction point V on to the xy plane. The backprojection data may also be obtained as described in connection with FIGS. 6 and 7. As described above, CPU 53 can determine the overlap or a separate overlap determining circuit connected to CPU 53 could be provided.

With respect to a voxel V2 in the overlapping region, the x-ray beams from the two focal spots overlap, so data Back(I,k) is obtained by backprojection with the weighting in accordance with Equation (3) after the prescribed processing of the projection data are obtained using the x-ray beam from focal spot F(k). Data Back(I,k+1) is obtained by backprojection with weighting in accordance with Equation (3) in the same way as the data obtained by the x-ray beam from focal spot F(k+1). Data Back(I) of the backprojection of this voxel V2 is obtained by weighting and adding the two data Back(I,k) and Back(I,k+1) in accordance with Equation (5):

$$Back(I)=\alpha \cdot Back(I,k)+(1-\alpha) \cdot Back(I,k+1) \quad (5)$$

where $\alpha=0.5+\{|(\text{z-coordinate of point CF})-(\text{z-coordinate of reconstruction point})|\}/WZ$, CF is a point where the two beams intersect and WZ is the range in the z-axis direction of backprojection of the two data or width of the overlap area. If this range is the overlapping region itself, it would be as shown in FIG. 8, being determined by the positional relationship of the focal spot and the voxel. The weighting of the projection data and/or the backprojection data are performed by circuits 52 and 56.

Thus, the CT data V(x,y,z) of voxel V2 is obtained in accordance with Equation (6) by integrating the backprojection data Back(I) over all of the views:

$$V(x,y,z) = \sum_{1}^{\text{views}} Back(I) \quad (6)$$

Although in the above weighted addition of the two data Back(I,k) and Back(I,k+1) was performed using a weighting coefficient α, it may be determined other than as given in Equation (4) and could be any weighting coefficient determined by the positional relationship between the focal spot position and the reconstruction point, or α could be a fixed value, such as 0.5 or 0.7, determined, for example, empirically.

Also, although, in Equation (4), the two (backprojected) convolved data D (channel, row) were backprojected to obtain Back(I,k) and Back(I,k+1), then respectively weighted and added, it would be possible to perform backprojection after weighting and adding in accordance with Equations (7) and (8):

$$D'(I)=\alpha \cdot D(k)+(1-\alpha) \cdot D(k+1) \quad (7)$$

$$Back(I)=1/W^2 \cdot D'(I) \quad (8)$$

Conventionally, with regard to the helical pitch, it is necessary that the intersection of the x-ray beam with respect to the center of the channel in the topmost row of the detector and the x-ray beam with respect to the center of the channel in the bottom-most row of the detector should be positioned outside the region where the subject is located. A second modification of the first embodiment of the invention, using extrapolation processing to eliminate this requirement, improving the image quality and the helical pitch, will be described. FIG. 5(b) shows the reconstruction processor 12 includes an extrapolation circuit 55. This circuit can be implemented hardware or software, in the same manner as described above. The operation of circuit 55 will be described with reference to FIGS. 9(*a*) and 9(*b*).

For backprojection of the projection data obtained by the linear interpolation of four data as described above with respect to voxels entirely within the effective field of view, the point of intersection described above should be located outside the center of the outer edge voxels of the effective field of view. From this condition alone the helical pitch becomes slightly larger. For example, under the same conditions as described above, a pitch P=13.72 mm is obtained.

Of course, it is to be assumed that backprojection will not be performed with respect to the region where linear interpolation of four data cannot be performed. It is thus possible to make the helical pitch larger, neglecting the drop in image quality in the vicinity of the outer edge of the FOV. However, if, when the z-coordinate of the point of intersection with the detector surface of the straight line (x-ray path) passing through the x-ray focal spot and the center of the voxel is outside (above) the uppermost row or (below) lowermost channel row center of the detector, extrapolation of the data of the upper or lower two rows/two channels of the detector is performed, backprojection data can be compiled. Better image quality is obtained.

Figure 9A:
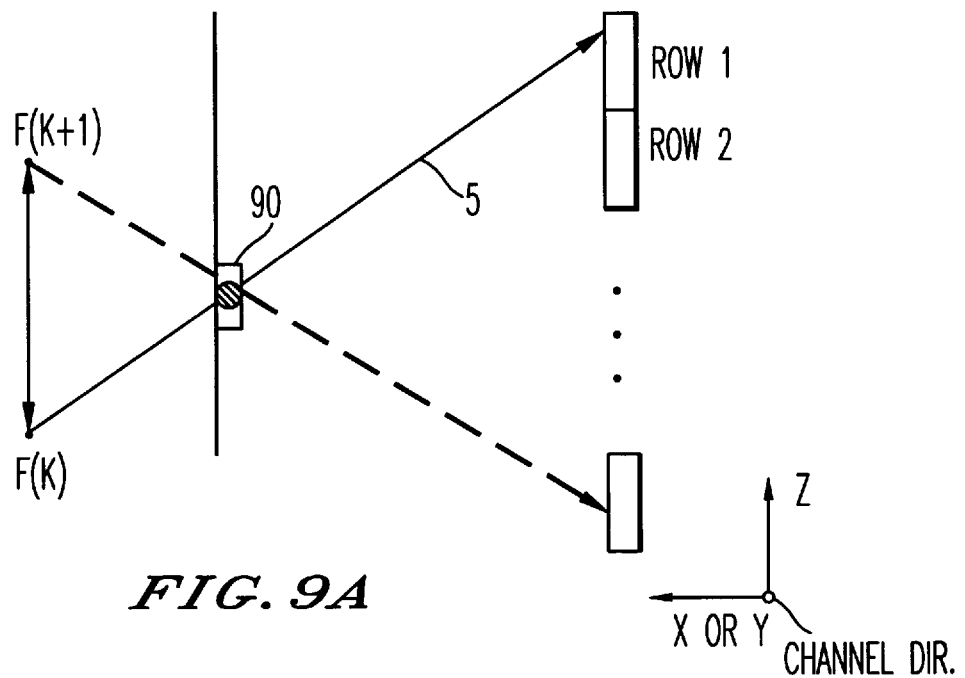
FIGS. 9(a) and 9(b) are diagrams illustrating extrapolation processing according to the invention.
Figure 9B:
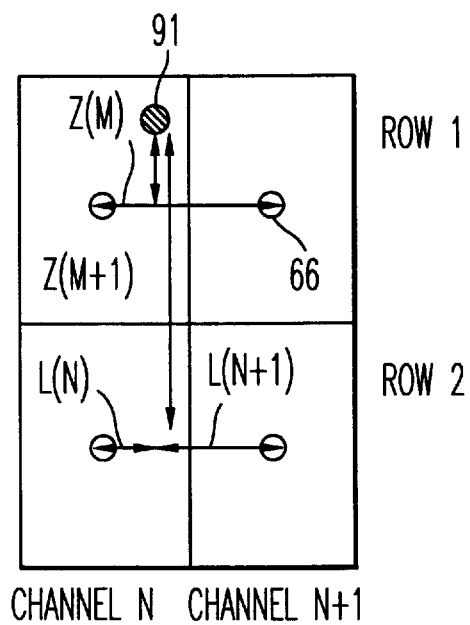

For example, FIG. 9(*a*) is a view, seen from the direction perpendicular to the z-axis, of the relationship between the x-ray beam and reconstruction voxel located next to the FOV edge in a given phase. Consider backprojection at voxel 90. If the straight line connecting focal spot F and the center of voxel V is extended, its point of intersection with the detector surface is point 91 (see FIG. 9(*b*)). In the channel direction, point 91 is considered on the n and n+1 channels; in the z-axis direction, point 91 is on the first row. Clearly, point 91 is above the z-coordinate of the center of the topmost edge detector row 1. Accordingly, projection data Back(I) are obtained by extrapolating, with the reciprocal of the distance, the four data from the n and n+1 channels of the first and second rows in accordance with Equation (9):

$$\text{Back}(I) = \frac{-Z(1)}{Z(2)-Z(1)} \left[ \frac{L(n+1)}{L(n+1)+L(n)} D(n,2) + \frac{L(n)}{L(n+1)+L(n)} D(n+1,2) \right] + \frac{-Z(2)}{Z(2)+Z(1)} \left[ \frac{L(n+1)}{L(n+1)+L(n)} D(n,1) + \frac{L(n)}{L(n+1)+L(n)} D(n,1) \right] = \frac{-Z(m)}{Z(m+1)-Z(m)} \left[ \frac{L(n+1)}{L(n+1)+L(n)} \right] + \frac{Z(m+1)}{Z(m+1)-Z(m)} \left[ \frac{L(n)}{L(n+1)+L(n)} \right] \quad (9)$$

where Z(1) and Z(2) are the distances in the z-direction to the point 91 from the centers of the row m and m+1 channels, and L(n), L(n+1) are the distances in the xy plane to the point 91 from the centers of the n and n+1 channels. Extrapolation is carried out in the same way when the point of intersection is below the channel center of the bottommost row of the detector, substituting Z(1) for Z(N) and Z(2) for Z(N−1) in Equation (9).

According to the second modification of the first embodiment, when performing extrapolation for one detector row, the helical pitch P can be defined by Equation (10), making it possible to obtain P=16.72 mm.

$$P \leq \text{Thick} \cdot ((N+I)/2 - 0.5) \cdot (FCD - FOV/2)/FCD \cdot 2 \quad (10)$$

where I is the extent of extrapolation. The pitch is made about 22% larger, thereby shortening the time required for scanning.

Up to this point, extrapolation for one detector row taking I=1 in Equation (10) has been described. However, the range of extrapolation is not restricted to this example. If image quality deterioration in the vicinity of the edge of the effective field of view FOV can be permitted, the value of the parameter I in Equation (10) can be made larger as I=2, I=3, etc. However, if the extrapolation is too great, image quality may in fact deteriorate, so it is preferable to determine the range (boundary) of extrapolation backprojection data beforehand, and, if the helical pitch exceeds this range, to provide boundary data outside this range. That is, values at the boundary in Z(2), Z(1) in Equation (9) may be input. The values input depend upon the purpose of the test. For example, for a lung test I=2, or for a head test I=1.

Up to this point, a method has been described of linear extrapolation of four data with the reciprocal of the distance. However, it would be possible to used non-linear extrapolation of four data or linear or non-linear extrapolation of 6, 8, . . . 2N data using the data of 3, 4, . . . N rows in the z-axis direction.

In the extrapolation processing described above, extrapolation was employed when the point of intersection was outside the detector center at the extreme edge, but the following steps [1]–[3] could also be employed:

[1] Having a row of dummy data above and below the data of the row N in each view when scanning; or

[2] Extrapolating the data one row at a time above and below, using the data of the Nth row in each view.

For example, virtual 0-th and (N+1)th row data can be extrapolated in accordance with the following Equations (11) and (12) from the first and second row and (N−1)th and Nth row of, for example, channel n:

$$D(n,0)=2 \times D(n,1)-D(n,2) \quad (11)$$

$$D(n,N+1)=2 \times D(n,N)-D(n,N-1) \quad (12)$$

[3] The data to be subjected to backprojection are found by performing interpolation processing as described above in the first embodiment, considering the data of the detector as consisting of a total of N+2 rows, including the virtual detector rows, i.e., the 0-th and (N+1)th rows calculated in [2] above. In this example, one row was added in each case above and below to compile N+2 virtual detector rows, but, by further increasing the number of virtual detector rows, it would be possible to use Equation (10) with I=1 increased to I=2, I=3, etc. The extrapolation using the dummy data is carried out by extrapolation circuit 55.

With the method combining this extrapolation processing and interpolation processing, the fixed processing of the overlap area interpolation can be performed with high speed using ordinary hardware; the extrapolation uses the same processing as the interpolation, so the system can be implemented in a low-cost configuration without the need for special hardware for extrapolation, such as by gate array 52 of FIG. 5(*a*).

In the above processing according to the first embodiment, image reconstruction is performed by scanning with a fixed helical pitch and carrying out backprojection of data obtained by prescribed processing to perform interpolation of the projection data. However, the processing of the first embodiment can also be applied to Feldkamp reconstruction in conventional scanning. Also, the processor 12 can perform both interpolation and extrapolation, as shown in FIG. 5(*b*).

A second embodiment of the invention will now be described. Where the system layout, method of compilation of the backprojection data, two-data backprojection processing onto the beam overlap region, and extrapolation processing are the same as in the case of the first embodiment, a description thereof is omitted.

In the two-data backprojection processing on to the beam overlap region described in the first embodiment, two projection data obtained from the two focal spots, namely, the focal spot on the kth revolution and the focal spot on the (k+1)th revolution, are backprojected with respect to a single voxel, weighted and added. Even though backprojection is performed by compiling virtual backprojection data by interpolation or extrapolation of four data, since the projected data or backprojected data are all compiled by interpolation or extrapolation, an error appears due to the error of the interpolation/extrapolation itself or due to the error generated when changing over between detector rows or channels employed for the interpolation/extrapolation in adjacent views, so a slight artifact may be generated. In the second embodiment, the helical pitch P is devised such as to reduce the artifact created by such changeover.

When determining the helical pitch P, in accordance with the custom for single-slice CT, this is determined so as to satisfy Equation (10) above and Equation (13):

$$P = \text{Thick} \cdot M \text{ (where } M \text{ is an integer)} \tag{13}$$

For example, under the conditions of the first embodiment, P=16 mm. However, if the helical pitch is an integral multiple of the basic slice thickness as in Equation (13), the changeover is performed with a timing representing an integral subdivision of a single revolution of 360°, so the same phenomena will always be produced at the same phase however many times revolution has taken place.

Figure 10A:
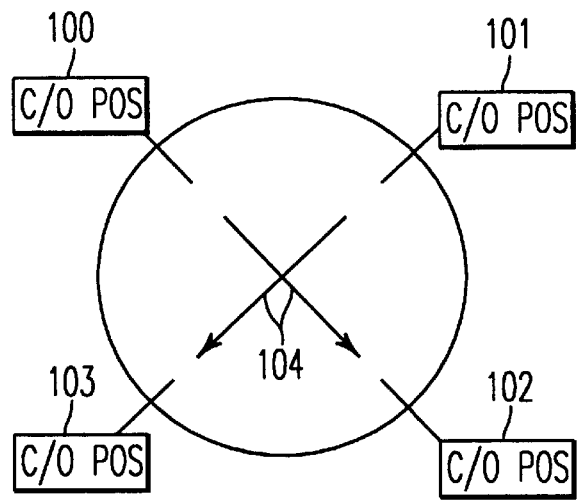
FIGS. 10(a), 10(b) and 10(c) are diagram illustrating the occurrence of an artifact due to changeover between the kth revolution and the (k+1)th revolution of projection data acquired by helical scan with the conventional helical pitch.
Figure 10B:
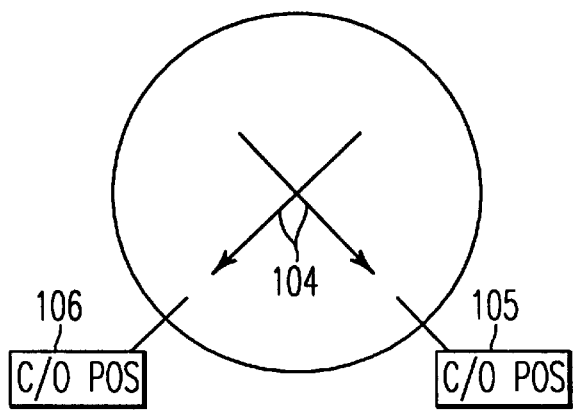
Figure 10C:
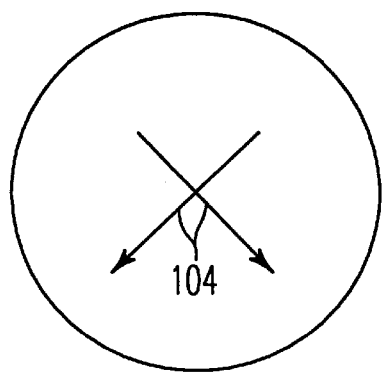

For example, FIGS. 10(a)–10(c) show the effect of the gap resulting from changeover of detector row used when the projection data is found by fourpoint interpolation, in order to achieve backprojection in respect of a particular voxel. FIG. 10(a) is a diagram of the angle (direction) produced by the gap resulting from changeover produced by the lower x-ray focal spot F(N) from the reconstruction plane, with 100–103 indicating the changeover positions and 104 indicating the artifact directions; FIG. 10(b) is a diagram of the changeover gap produced by the upper focal spot F(N+1) after one revolution, with changeover positions 105 and 106. Since the changeover occurs with the same phase (angle of rotation), backprojection including any error is effected in the same direction, so the artifacts are superimposed and, even though backprojection and weighted addition of two data from two focal spots is performed at a single voxel, there is no possibility of the artifact being attenuated. FIG. 10(c) shows the results of the weighting addition.

Accordingly, in the second embodiment, the helical pitch is determined so as to satisfy Equations (10) and (14):

$$P = \text{Thick} \times J \text{ (where } J \text{ is not an integer)} \tag{14}$$

That is, the helical pitch is set to a non-integral multiple of the basic slice thickness. The system controller 8 and the gantry/bed controller 9 control the pitch during scanning of the ring 2 to be a non-integral multiple of the slice thickness.

Figure 11A:
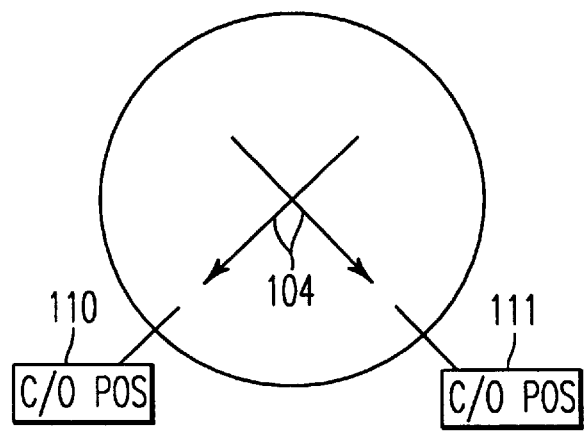
FIGS. 11(a), 11(b) and 11(c) are diagrams illustrating mitigation of an artifact produced by changeover between the kth revolution and the (k+1)th revolution of projection data acquired by helical scan with helical pitch according to the invention.
Figure 11B:
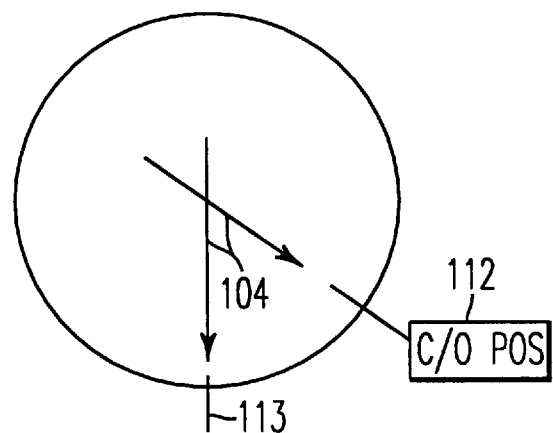
Figure 11C:
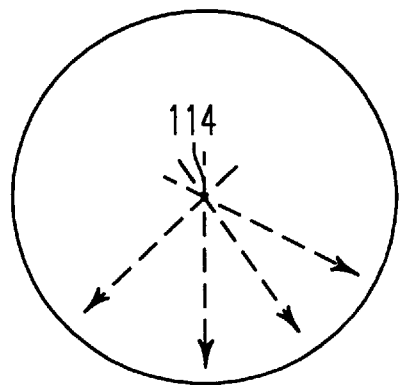

The direction of the gap produced by the changeover described above at this time is as shown in FIGS. 11(a)–11(c). FIG. 11(a) results from the x-ray focal spot below the reconstruction plane, and shows changeover positions 110, 111 and artifacts 104; FIG. 11(b) results from the x-ray focal spot above the reconstruction plane, and FIG. 11(c) shows the results of the weighted addition. Since the directions where changeover occurs are offset as between the upper side and the lower side, they cancel each other out, with the result that the artifact 114 is distinctly weakened.

For example, if the data when using an integral pitch having an artifact at the changeover is [0010000], weighting subsequent scans by ½ and then adding gives [0010000], since the artifact data is the same during each scan. The artifact is not attentuated. The data when using a nonintegral pitch will not be the same for subsequent scans. For example, for data [00100000] and [00000100], weighting by ½ and adding gives [00½00½00]. The artifact is weakened, or may be canceled by thresholding.

It should be noted that helical pitch is not restricted to the condition described above. It is important that the phase where changeover occurs is determined such that it is offset above and below on either side of the reconstruction plane; at least the condition that the helical pitch is a non-integral multiple of the basic slice thickness is important. For example as well known in the case of fan-beam reconstruction, when a so-called half reconstruction of 180° + fan angle is combined with the Feldkamp reconstruction, Equation (10) is not a necessary condition (it is applied to 360° backprojection).

Also, in the ordinary clinical application, the effective field-of-view FOV changes with the part that is the subject of the imaging, the abdomen being of a medium size while the head is usually the small size. Although the value in Equation (10) of the helical pitch is fixed at ω=FOV/2=120 mm, it is not in fact fixed but varies in accordance with the FOV size of the part that is the subject of imaging. Because of this, a large helical pitch may be selected when the imaging region is of small size. For example, if the FOV size is made 120 mm instead of 240 mm, when performing 360° reconstruction, in accordance with Equation (10), the upper limit of P changes from 16.72 mm to 19.36 mm. Choosing a suitable value from Equation (14), P changes from 16.5 mm to 18.5 mm. Or conversely, the FOV size may be determined from the helical pitch. The present invention uses the non-integral pitch when scanning regions both when FOV is changed and when remains the same, or substantially the same.

Image reconstruction is then performed by the same technique as in the case of the first embodiment, carrying out helical scanning with helical pitch determined as above.

Since a large gap exists between the directions of the reconstruction commencement angle and reconstruction termination angle in the case of 360° reconstruction, a problem exists that this gap results in the formation of a clearly visible streak on the image. Also, if a two-data backprojection process (as described in the first embodiment) is performed, a image of high density resolution and low noise can be obtained. On the other hand, the effective slice thickness is rather large, since data are used that have a large inclination with respect to the cone angle. It is sometimes the case in clinical practice that the slice thickness is more important than noise. A third embodiment of the invention that prioritizes slice thickness will therefore be described.

It backprojection can be performed using an x-ray beam of small beam angle, i.e., a small cone angle with respect to the xy plane, the effective slice thickness is decreased. Consequently, for voxels within border area in the region of overlap of the x-ray beams from x-ray focal spot F(k) and F(k+1) of the kth revolution and (k+1)th revolution, i.e., a region for which the x-ray beam cone angles from the x-ray focal spots F(k) and F(k+1) of the kth revolution and (k+1)th revolution respectively are practically the same, two-data backprojection is performed. For voxels outside this overlap region, even if the two x-ray beams should still happen to overlap, backprojection is performed selecting only the projection data of the x-ray beam of smallest cone angle.

Figure 12A:
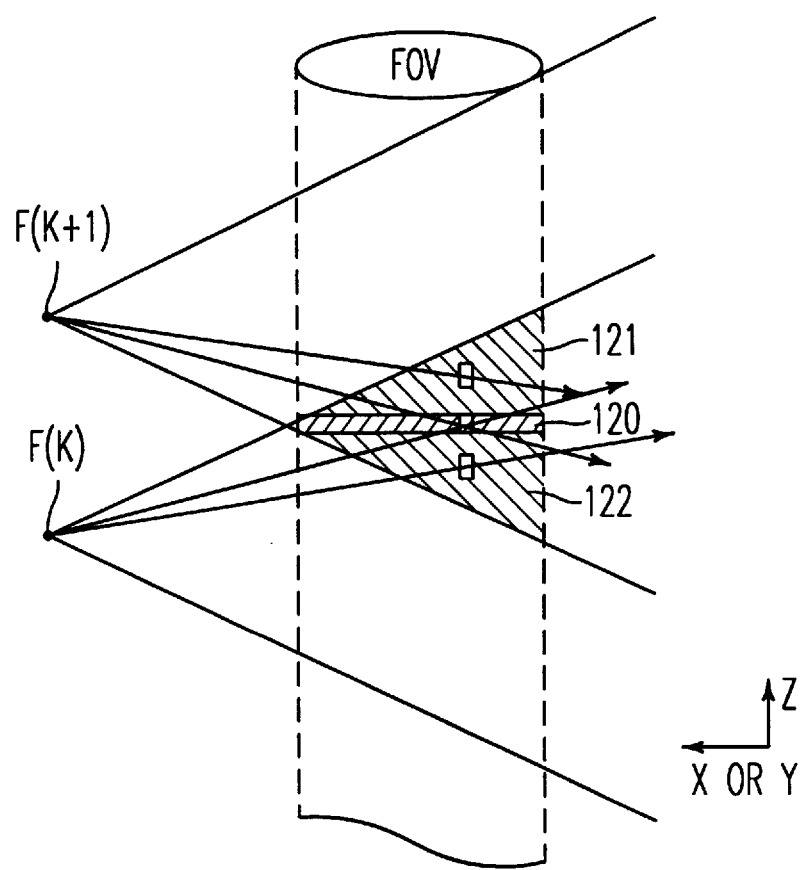

FIG. 12(a) shows an example of an area 120 defined as the border area. As described above, the CPU 53 shown in FIGS. 5(a) and 5(b) determines the border area within the overlap area, but a separate circuit may be provided. In this case, backprojection is performed on the projection data obtained by x-rays from focal spot F(k+1) of small cone angle to voxels within an upper region 121 outside the border area but within the overlapping region, and backprojection is performed on projection data obtained by x-rays from F(k) to voxels within the lower region 122 outside the border area but within the overlapping region. However, for voxels within the border area where the cone angles from the two focal spots are practically the same, Back(I,k), and Back(I,k+1) are obtained by backprojection on to the respective reconstruction points from the two focal spots F(k) and F(k+1) to voxels within the border area where the cone angles from the two focal spots are practically equal (as shown in FIG. 12(a)), and backprojection value Back(I) to the reconstruction point is obtained by adding and averaging, by weighted addition, or another method, of these respective values.

In FIG. 12(a) the voxel is considered to be in the border area if its center lies in the border area. However, other criterion for determining the voxels in the border area are possible. For example, when $\alpha=90°$, the height of the border (width in z-direction is P×90/360=P/4=18.4/4=4.625.

Figure 12B:
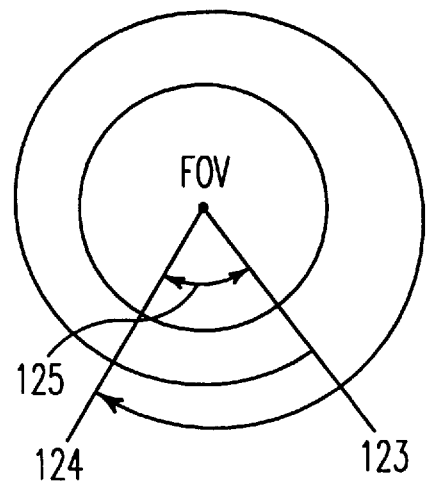

FIG. 12(b) shows a top view of a reconstruction plane with reconstruction commencement angle 123 ($\theta_s$), reconstruction completion angle 124 ($\theta_e$), and the overlap angle 125 ($\alpha$). The difference between angle 123 and angle 124 is $\alpha+2\pi$. Considering a given reconstruction plane, if the difference between the cone angles of the upper and lower focal spots on either side of the reconstruction plane is large (See FIG. 12(a)), backprojection is performed with respect only to the beam of smaller cone angle. If on the other hand the difference is small, backprojection is performed from both the upper and lower focal spots, and the results are weighted and added. Specifically, rather than reconstructing a single tomographic image with projection data corresponding to 360°, weighting and adding are performed for the overlapping region using the upper and lower overlapping data corresponding to 360°+$\alpha$, to compile 360° reconstructed data, which is then used for reconstructing a single tomographic image. When performing weighting and addition, the weights may be changed linearly or non-linearly depending on this angle.

This angle-dependent weighting of the backprojection data now be described. Angle-dependent weighting has advantages when the effective slice thickness is thin, and it is easy implement in hardware. Also, the angle and position dependent weighting has advantages of a better S/N and better low contrast.

Figure 13A:
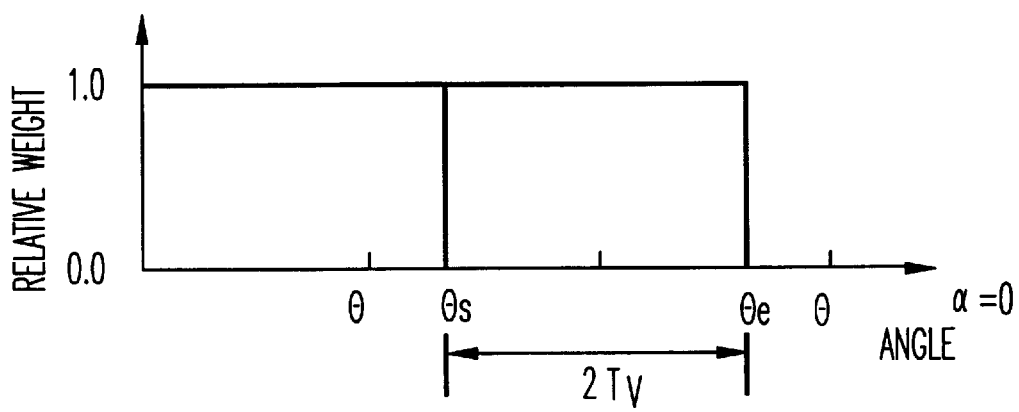
FIGS. 13(a), 13(b) and 13(c) are diagrams illustrating weighting factors according to the invention.
Figure 13B:
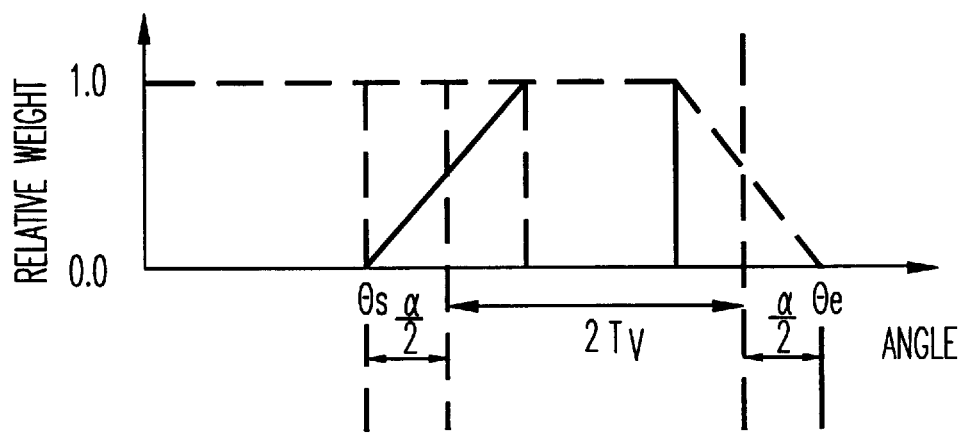
Figure 13C:
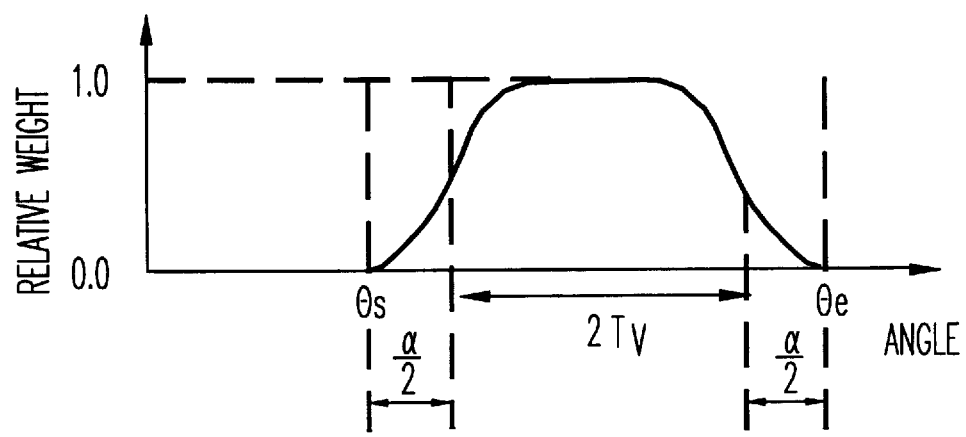

FIGS. 13(a)–(c) are views showing how data collected at an angle to the horizontal axis in FIG. 12(b) are backprojected with the relative weight shown on the vertical axis. FIG. 13(a) is a view given for reference purposes and shows a method wherein, in the conventional backprojection method, data (even in the overlapping region of smaller cone-angle) are selected and backprojected. The angle of backprojection is 2$\pi$, i.e., 360° where $\alpha=0$. Here, $\theta_s$ and $\theta_e$ correspond to the starting and ending backprojection angles. FIGS. 13(b) and 13(c) show a method of backprojection in which the angle of overlap is taken as $\alpha$ and weighting is applied to the data obtained on two rotations. In FIG. 13(b) linear weighting is applied while in FIG. 13(c) non-linear weighting is applied. With the object of suppressing the effect of the gap, the weighting function should ideally be a non-linear function that is continuous, whose first derivative is also continuous, and which has a minimum where the first derivative has a maximum.

According to the invention, the clearly apparent artifact produced in the direction of commencement of reconstruction and the direction of termination of reconstruction can be removed or attenuated, improving the image. The shape of the border area and the range (angle) of the overlap region are not restricted to the above and could show dependence on position within the plane as in FIG. 12(c). Illustrated in FIG. 12(c) are border region 127 and upper and lower overlap regions 126 and 127. Further, there is no restriction of linear or non-linear weighting and addition of two beams in an overlap region. The weighting could be a constant weighting and additive averaging could be employed. In the system for weighting and backprojection according to this embodiment, the angle-dependent weighting may be performed circuits 52 and 56.

Also, although in the above description two (backprojected) convolved data D (channel, row) were backprojected to obtain Back(I,k) and Back(I,k+1), which were then weighted and added, the backprojection could be performed after the weighting and addition. Specifically, Equations (15) and (16), obtained by transforming Equations (4) and (5), could be employed:

$$D'(I)=\beta \cdot D(k)+(1-\beta) \cdot D(k+1) \qquad (15)$$

$$Back(I)=1/W^2 \cdot D'(I) \qquad (16)$$

The difference between the two types of methods of weighting the region where the two sets of x-rays overlap will now be explained in more detail.

Figure 14A:
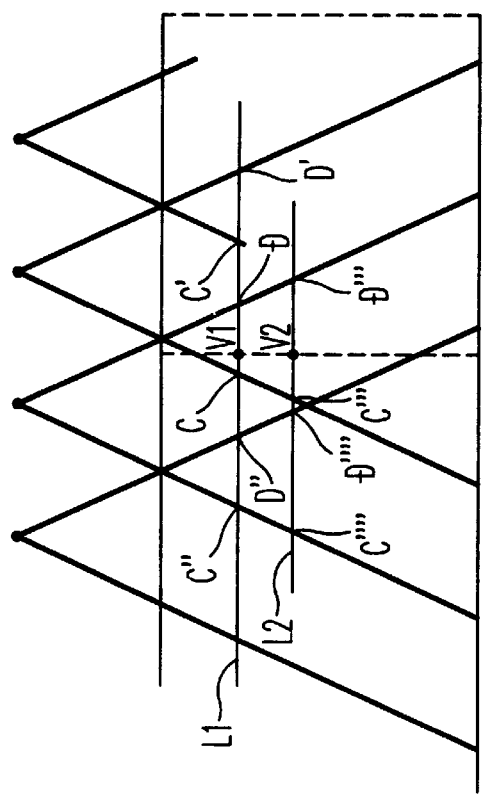
FIGS. 14(a)–14(d) are diagrams illustrating weighting factors according to the invention.
Figure 14B:
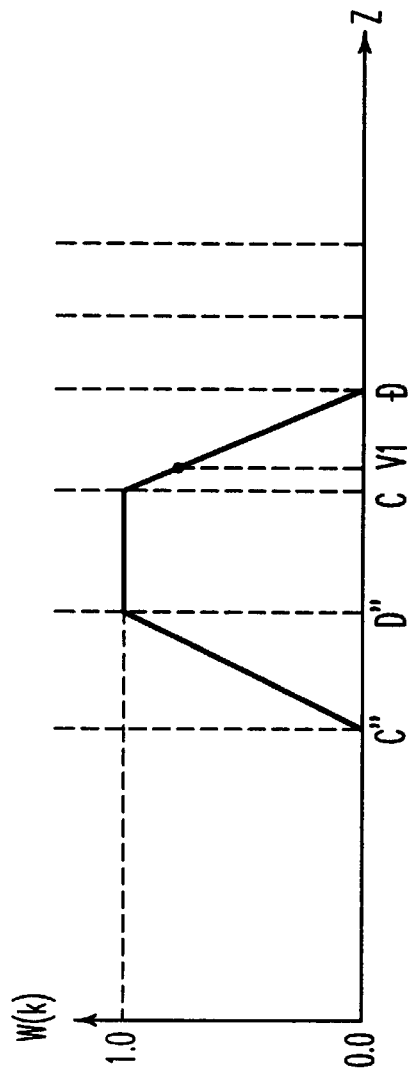
Figure 14C:
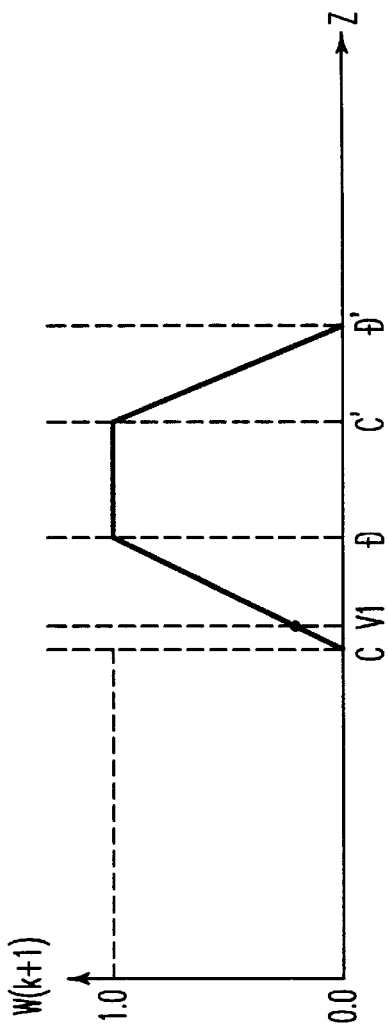

The first situation is where the weighting of the data of each voxel in the plane of the slice has positional dependence for data of a certain angle. This will be described in reference to the method shown in FIG. 8 and used in the first embodiment. Linear weighting is shown, but other types of weighting as described above could be used. Consider, for example, two voxels V1 and V2 which are in the same axial plane (i.e. whose z-coordinates are the same) as shown in FIG. 14(a). X-ray beams for the two focal spots F(k) and F(k+1) are incident on voxels V1 and V2. Now consider the straight line L1 parallel to the z-axis (axis of rotation) and passing through voxel V1. Let the points of intersection of this straight line L1 with the edges of the x-ray beams emitted from F(k) and F(k+1) be D and C. The relative weights W(k) when the data of focal spot F(k) are backprojected onto each voxel on this straight line are then as shown in FIG. 14(b). The weights W(k+1) when the data of focal spot F(k+1) corresponding to the voxel V1 are backprojected are as shown in FIG. 14(c).

Figure 14D:
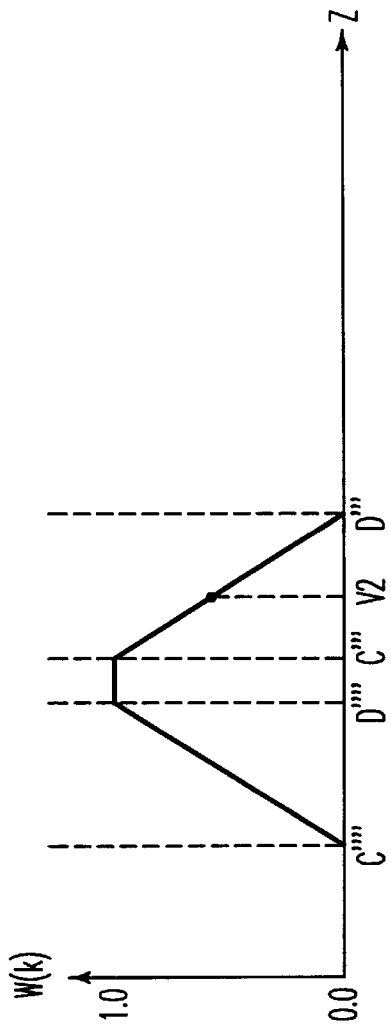

Likewise the weights W(k), W(k+1) of the focal spots F(k), F(k+1) onto the voxel V2 on the straight lien L2 passing through voxel V2 which is in the same axial plane as voxel V1 can be determined. The weights W(k) are shown in FIG. 14(d). As apparent from FIG. 14(b) and FIG. 14(d), the weights W(k) of V1 and V2 are different, i.e., even if the data obtained from the same focal spot are backprojected in the same axial plane, the weights of the respective beams will be different when backprojected, depending on the positional relationship of the voxels and focal spot within the axial plane.

Figure 15A:
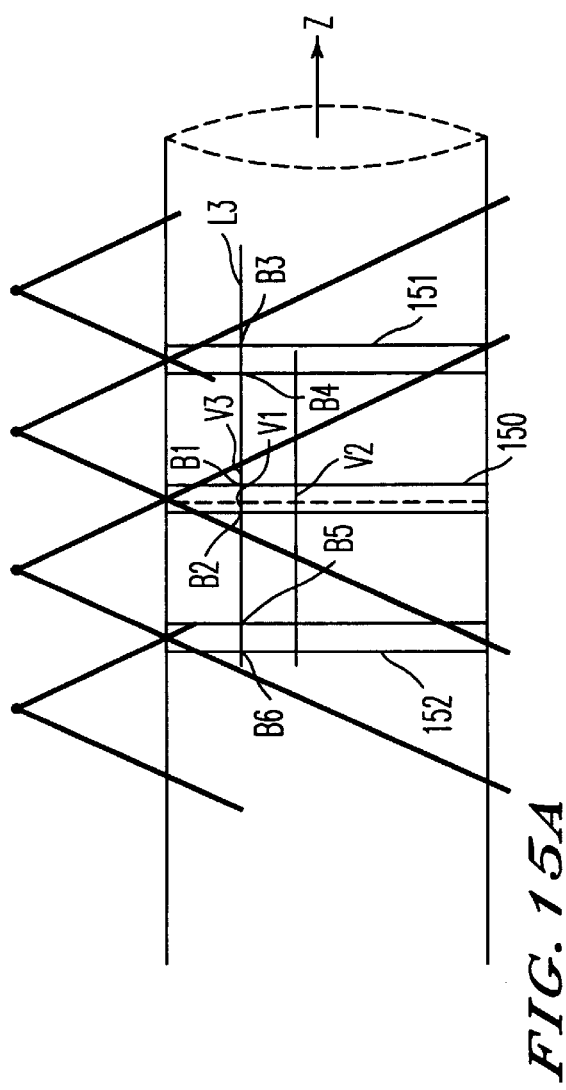
FIGS. 15(a)–15(d) are diagrams illustrating weighting factors according to the invention.

The second situation, when the weight of all the voxels in the slice is the same for data of a given angle, corresponding to the method described in reference to FIG. 12, will now be explained, with reference to FIG. 15(a). Consider voxels V1 and V2 that are in the same axial plane and voxel V3 which is in a different axial plane. Each of these three voxels is irradiated by the x-ray beams from the two focal spots F(k) and F(k+1).

According to the invention, as described above, backprojection using the two beams is effected only with respect to the restricted overlap or border region 150, so only backprojection data obtained from the focal spot position having the smaller cone angle at V3 is backprojected. Specifically, consider straight line L3 parallel to the z-axis and passing through voxel V1. The region where backprojection is performed with the two data from the overlapping focal spots is the border area 150 in FIG. 15(a), and the points of intersection of this straight line L3 with the border area 150 are B1 and B2. The points of intersection of line L3 with the adjacent border regions 151 and 152 are B3, B4 and B5, B6, respectively.

Figure 15B:
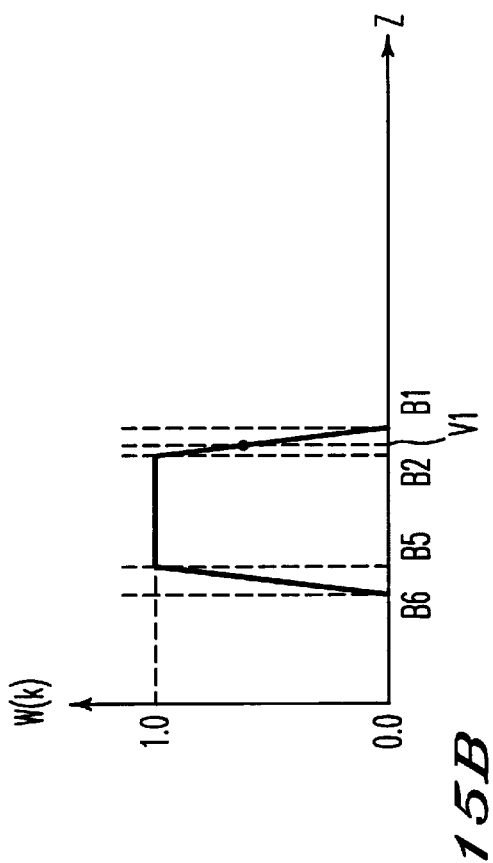
Figure 15C:
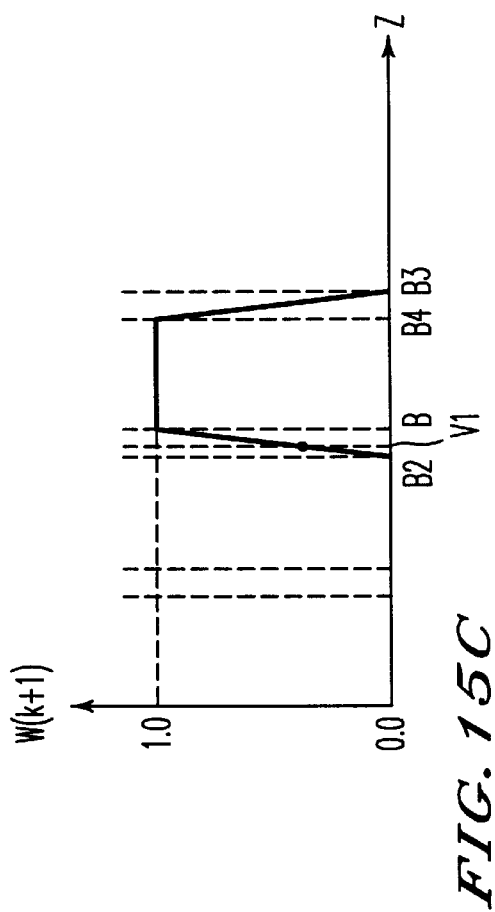
Figure 15D:
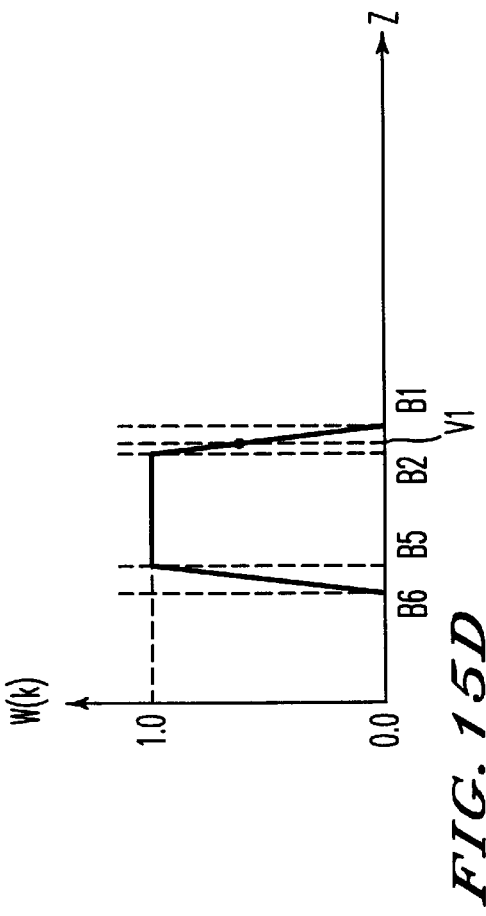
Figure 16:
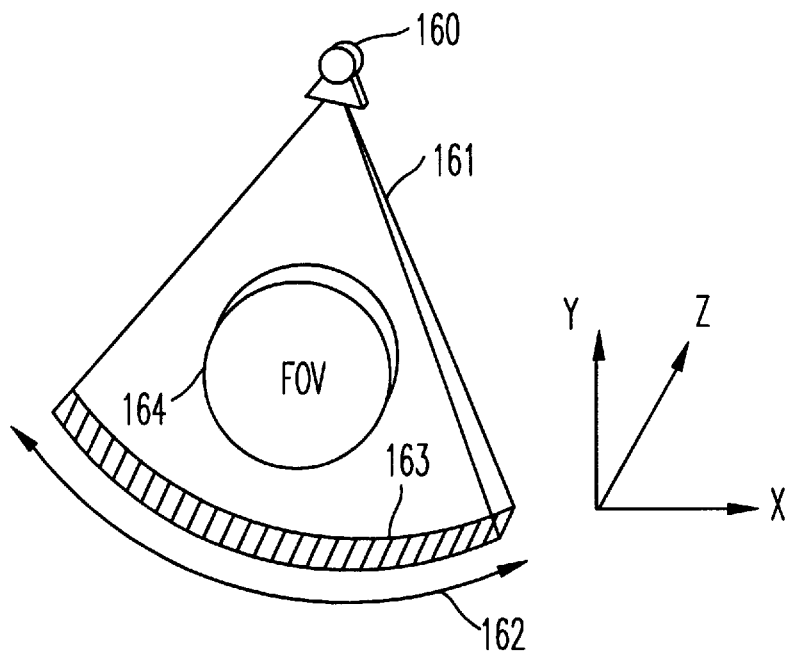
FIG. 16 is a perspective view of a one-dimensional array type x-ray detector.
Figure 22:
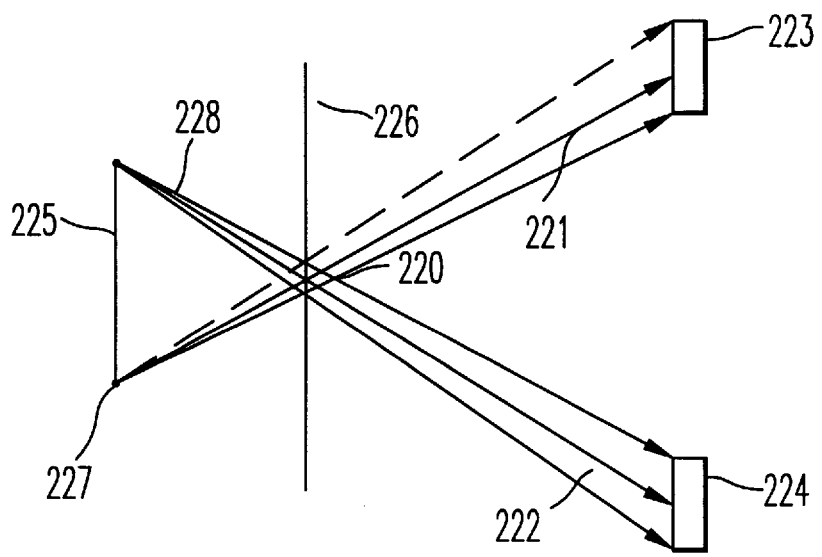
FIG. 22 is a diagram illustrating a conventional method of determining helical pitch.

The weights W(k) when the data of focal spot F(k) is backprojected onto voxel V1 are shown in FIG. 15(b) and the weights W(k+1) when the data of focal spot F(k+1) is backprojected are shown in FIG. 15(c). It should be noted that the region where the two data are weighted and backprojected is different from that in FIGS. 14(a)–14(d).

Also the weights W(k), W(k+1) of the focal spots F(k), F(k+1) onto voxel V2, and other voxels on the straight line passing through voxels V1 and V2, which is in the same axial plane (i.e. has the same z-coordinate) are likewise shown in FIG. 15(b) and FIG. 15(c) from the points of intersection with the border area. That is, since the weights do not depend on the spreading of the beam as described with reference to FIGS. 14(a)–14(d), i.e., they do not depend on the position of the voxel in the axial plane, when backprojected for all the voxels in the same axial plane, the weights of the two beams are the same. That is, an angle-dependent weighting equation as in FIG. 15(b) or FIGS. 13(b) and 13(c) is possible. This shows that, the CT system according to the invention, when implemented by hardware, can be implement with a straightforward construction and small cone angle data can be utilized for the image reconstruction, so image quality is improved.

With such a system construction an image can be reconstructed by backprojection with 2-data backprojection method, by scanning with helical pitch, weight and extrapolation, or by scanning with helical pitch and compiling backprojection data by the backprojection data compilation method.

The present invention is not restricted to the embodiments described above but can be put into practice in various modified ways. The scope of the invention is defined by the appended claims. For example, while the invention has been discussed as having several embodiments, the features and advantages of each of the embodiments may be combined into a single system, as shown in FIG. 5(b), allowing a user to utilize all of the features and advantages of the invention.

What is claimed as New and Desired to be Secured by Letters Patent is:

1. A computed tomography system, comprising:
   an x-ray source;
   a detector array having a plurality of detection elements and disposed to receive x-rays emitted from said xray source; and
   a projection data circuit connected to said detector array;
   a multi-row interpolation circuit connected to said projection data circuit; and
   a backprojection circuit connected to said multi-row interpolation circuit.

2. A system as recited in claim 1, wherein said multi-row circuit is a 2N-point interpolation circuit, where N is an integer greater than 1.

3. A system as recited in claim 1, wherein said multi-row interpolation circuit comprises:
   an x-ray path calculating circuit; and
   a distance measuring circuit connected to said x-ray path circuit.

4. A system as recited in claim 1, comprising:
   a position-dependent and angle-dependent weighting circuit connected to said backprojection circuit.

5. A system as recited in claim 1, comprising:
   a position-dependent and angle-dependent weighting circuit connected to said projection data circuit.

6. A system as recited in claim 1, comprising:
   a rotating member;
   said x-ray source mounted on said rotating member;
   said detector array mounted on said rotating member; and
   means for rotating said rotating member to produce a helical pitch that is a non-integral multiple of a slice thickness of an image of a subject, having a portion with a field of view of substantially a given size, over said portion.

7. A system as recited in claim 1, comprising:
   a rotating member;
   said x-ray source mounted on said rotating member;
   said detector array mounted on said rotating member; and
   means for attenuating changeover artifacts using said rotating member to produce a helical pitch that is a non-integral multiple of a slice thickness of an image of a subject, having a portion with a field of view of substantially a given, over said portion.

8. A system as recited in claim 1, comprising:
   means for producing a helical pitch of said system variable with respect to an effective field-of-view.

9. A system as recited in claim 1, comprising:
   a z-coordinate weighting circuit connected to said projection data circuit; and
   a convolution circuit connected to said weighting circuit.

10. A system as recited in claim 1, wherein:
    said detector array comprises a plurality of rows; and said multi-row interpolation circuit comprises:
    means for calculating an x-ray path from said x-ray source through a voxel in a subject being irradiated by said x-ray source to a point on said detector array; and
    means for interpolating projection data, from said projection data circuit, of selected detector elements associated with said point from at least two rows of said detector and producing interpolation data.

11. A system as recited in claim 10, wherein said means for interpolating further comprises means for weighting said backprojection data.

12. A system as recited in claim 10, wherein said means for interpolating comprises:
    means for determining a distance in at least two directions of said point to a predetermined location in said selected detector elements;
    means for applying a first interpolation function to distances in a first direction; and
    means for applying a second interpolation function to distances in a second direction.

13. A system as recited in claim 10, wherein said means for interpolating comprises means for linearly interpolating said projection data using $$Back(I) = \frac{Z(m)}{Z(m+1)+Z(m)} \left[ \frac{L(n+1)}{L(n+1)+L(n)} D(n,m+1) + \frac{L(n)}{L(n+1)+L(n)} D(n+1,m+1) \right] + \frac{Z(m+1)}{Z(m+1)+Z(m)} \left[ \frac{L(n+1)}{L(n+1)+L(n)} D(n,m) + \frac{L(n)}{L(n+1)+L(n)} D(n,m) \right]$$

where L(n) and L(n+1) are distances in a row direction from centers of detector elements n and n+1 in rows m and m+1 of said detector array to said point, and Z(m) and Z(m+1) are distances in a direction perpendicular to said row direction from said centers to said point.

14. A system as recited in claim 10, wherein said means for interpolating comprises:
means for determining a closest two detector elements to said point on said detector array in each of N rows; and
means for using projection data from said closest 2N detector elements to produce said interpolation data.

15. A system as recited in claim 14, wherein said system comprises:
means for determining respective first distances from a predetermined location in each of two of said detector elements in a first row of said detector array and respective second distances from said predetermined location in each of two detector elements in each of (N−1) rows adjacent to said first row;
wherein said means for interpolating produces said interpolation data using said first and second distances.

16. A system as recited in claim 1, comprising:
an x-ray beam overlap area determining circuit connected to said interpolation circuit.

17. A system as recited in claim 16, wherein:
said x-ray beam overlap area determining circuit comprises means for determining an overlap area of a first x-ray beam from a first irradiation point and a second x-ray beam from a second irradiation point; and
said backprojection circuit comprises:
means for producing first backprojection data for a first voxel of a subject irradiated by one of said first and second x-ray beams outside of said overlap area based upon only said one of said first and second x-ray beams; and
means for producing second backprojection data for a second voxel of said subject located in said overlap area and irradiated by both of said first and second x-ray beams based upon both of said first and second x-ray beams.

18. A system as recited in claim 17, wherein:
said means for producing said second backprojection data uses first projection data associated with a first x-ray path from said x-ray source through said second voxel of said first x-ray beam, and second projection data associated with a second x-ray path from said x-ray source through said second voxel of said second x-ray beam.

19. A system as recited in claim 18, wherein:
said means for producing said second backprojection data weights and adds said first and second projection data.

20. A system as recited in claim 18, wherein:
said means for producing second backprojection data respectively weights said first and second projection data using a first distance determined from said first and second x-ray paths, respectively, and produces first and second weighted data; and
said means for producing second backprojection data weights said first and second weighted data based upon a second distance between a point of intersection of said first and second beams and a reconstruction point associated with said second voxel and upon a width of said overlap area associated with said second voxel.

21. A system as recited in claim 20, wherein:
said means for producing second backprojection data weights said first and second data using $1/W^2$, where W is said first distance, and weights said first and second weighted data using $\alpha$ and $(1-\alpha)$, respectively, where $\alpha$ is said second distance divided by said width.

22. A system as recited in claim 1, comprising:
a multi-row extrapolation circuit connected to said interpolation circuit.

23. A system as recited in claim 5, wherein:
said multi-row extrapolation circuit is a 2N-point extrapolation circuit.

24. A system as recited in claim 22, wherein said multi-row extrapolation circuit comprises:
means for calculating an x-ray path from said x-ray source through a voxel in a subject being irradiated by said x-ray source to a point on said detector array one of above and below a predetermined location in an uppermost or lowermost row, respectively, of said detector array; and
means for extrapolating projection data, from said projection data circuit, of 2N selected detector elements and producing extrapolation data;
wherein said backprojection circuit produces backprojection data using said extrapolation data.

25. A system as recited in claim 24, wherein said means for extrapolating further comprises means for weighting said backprojection data.

26. A system as recited in claim 24, wherein said means for extrapolating comprises:
means for determining a closest two detector elements to said point on said detector array in each of N rows; and
means for using projection data from said closest 2N detector elements to produce said extrapolation data.

27. A system as recited in claim 24, comprising means for determining respective first distances from a predetermined location in each of two of said detector elements in a first row and respective second distances from said predetermined location in each of two detector elements in each of (N−1) rows adjacent to said first row;
wherein said means for extrapolating produces said extrapolation data using said first and second distances.

28. A system as recited in claim 22, wherein said extrapolation circuit comprises:
means for calculating an x-ray path from said x-ray source through a voxel in a subject being irradiated by said x-ray source to a point on said detector array one of above and below a predetermined location in an uppermost or lowermost row, respectively, of said detector array;
means for calculating extrapolation data from one of said uppermost and lowermost rows; and
means for interpolating projection data, from said projection circuit, and said extrapolation data to produce interpolation data;
wherein said backprojection circuit backprojects said interpolation data.

29. A system as recited in claim 28, wherein said means for calculating extrapolation data calculates said extrapolation data from dummy data from detector elements in a dummy row one of below and above said lowermost and uppermost rows, respectively.

30. A system as recited in claim 1, comprising:
an x-ray beam border determining circuit connected to said interpolation circuit.

31. A system as recited in claim 30, wherein said x-ray border determining circuit comprises:
means for determining an overlap area of a first x-ray beam from a first irradiation point and a second x-ray beam from a second irradiation point; and
means for determining a border region in said overlap area.

32. A system as recited in claim 31, comprising:
means for performing backprojection on a voxel in said border region using projection data from both of said first and second x-ray beams and on a voxel in said overlap area but outside of said border region using only one of said first and second x-ray beams.

33. A system as recited in claim 31, wherein said means for determining a border region determines said area as a region wherein cone angles of said first and second x-rays beams are substantially equal.

34. A computed tomography system, comprising:
an x-ray source;
a detector array having a plurality of detection elements arranged in rows and disposed to receive x-rays emitted from said x-ray source;
a projection data circuit connected to said detector array;
an x-ray beam overlap area determining circuit connected to said projection data circuit; and
a backprojection circuit connected to said projection data and x-ray beam overlap area determining circuits.

35. A system as recited in claim 34, comprising:
a rotating member;
said x-ray source mounted on said rotating member;
said detector array mounted on said rotating member; and
means for rotating said rotating member to produce a helical pitch that is a non-integral multiple of a slice thickness of an image of a subject, having a portion with a field of view of substantially a given size, over said portion.

36. A system as recited in claim 34, comprising:
a rotating member;
said x-ray source mounted on said rotating member;
said detector array mounted on said rotating member; and
means for rotating said rotating member to produce a helical pitch that is a non-integral multiple of a slice thickness of an image of a subject, having a portion with a field of view of substantially a given size, over said portion.

37. A system as recited in claim 34, comprising:
means for producing a helical pitch of said system variable with respect to an effective field-of-view.

38. A system as recited in claim 34, wherein:
said x-ray beam overlap area determining circuit comprises means for determining an overlap area of a first x-ray beam from a first point and a second x-ray beam from a second point; and
said backprojection circuit comprises:
means for producing first backprojection data for a first voxel of a subject irradiated by one of said first and second x-ray beams outside of said overlap area based upon only said one of said first and second x-ray beams; and
means for producing second backprojection data for a second voxel of said subject located in said overlap area and irradiated by both of said first and second x-ray beams based upon both of said first and second x-ray beams.

39. A system as recited in claim 38, wherein said second voxel is a common voxel.

40. A system as recited in claim 38, wherein:
said means for producing said second backprojection data uses first projection data associated with a first x-ray path from said x-ray source through said second voxel of said first x-ray beam, and second projection data associated with a second x-ray path from said x-ray source through said second voxel of said second x-ray beam.

41. A system as recited in claim 40, wherein:
said means for producing said second backprojection data weights and adds said first and second projection data.

42. A system as recited in claim 40, wherein said second voxel is a common voxel.

43. A system as recited in claim 40, wherein:
said means for producing second backprojection data respectively weights said first and second projection data using a first distance determined from said first and second x-ray paths, respectively, and produces first and second weighted data; and
said means for producing second backprojection data weights said first and second weighted data based upon a second distance between a point of intersection of said first and second beams and a reconstruction point associated with said second voxel and upon a width of said overlap area associated with said second voxel.

44. A system as recited in claim 43, wherein:
said means for producing second backprojection data weights said first and second data using $1/W^2$, where W is said first distance, and weights said first and second weighted data using $\alpha$ and $(1-\alpha)$, respectively, where $\alpha$ is said second distance divided by said width.

45. A computed tomography system comprising:
an x-ray source;
a detector array having a plurality of detection elements and disposed to receive xrays emitted from said x-ray source;
a projection data circuit connected to said detector array; and
a position-dependent and angle-dependent weighting circuit connected to said projection data circuit;
wherein said weighting circuit comprises at least one of:
means for varying weighting based upon a reconstruction angle of a reconstruction image produced by said system; and
means for varying weighting based upon a position of a voxel relative to a position of said x-ray source; and
wherein said means for vary weighting based upon a reconstruction angle comprises:
means for determining a cone angle of each of two x-ray beams emitted from two focal spots of said x-ray source about a reconstruction plane;
means for determining an region in an overlap area of said two x-ray beams;
means for performing backprojection outside of said region using one of said two beams having a smaller cone angle; and means for performing backprojection inside of said region using both of said two x-ray beams.

46. A system as recited in claim 45, wherein said weighting circuit comprises means for weighting based upon a reconstruction angle.

47. A system as recited in claim 46, wherein said means for weighting based upon a reconstruction angle weights based upon at least one of a reconstruction commencement angle, a reconstruction termination angle and an overlap angle.

48. A system as recited in claim 45, comprising:
a backprojection circuit connected to said weighting circuit.

49. A computed tomography system comprising:
an x-ray source;
a detector array having a plurality of detection elements and disposed to receive x-rays emitted from said xray source;
a projection data circuit connected to said detector array;
a position-dependent and angle-dependent weighting circuit connected to said projection data circuit;
means for determining a region in an overlapping area of two x-ray beams emitted from said x-ray source; and
means for weighting voxels located in said region and in a same axial plane with a same weight.

50. A computed tomography system comprising:
an x-ray source;
a detector array having a plurality of detection elements and disposed to receive x-rays emitted from said xray source;
a projection data circuit connected to said detector array; and
a position-dependent and angle-dependent weighting circuit connected to said projection data circuit;
wherein said weighting circuit comprises means for varying weighting based upon a position of a voxel and overlapping regions of x-ray beams emitted from said x-ray source.

51. A method of operating a computed tomography system having a detector with a plurality of detector elements arranged in rows, comprising:
obtaining projection data;
interpolating said projection data using a plurality of said detector elements from at least two of said rows; and
interpolating said projection data using 2N detector elements, where N is an integer greater than 1.

52. A method as recited in claim 51, comprising:
backprojecting using interpolated projection data.

53. A method as recited in claim 51, wherein said system comprises an x-ray source, said method comprising:
scanning first and second x-ray beams having an overlapping region over a subject; and
backprojecting using both of said first and second x-ray beams for a first portion of said subject in said overlapping region; and
backprojecting using one of said first and second x-ray beams for respective second portions of said subject outside of said overlapping region.

54. A method as recited in claim 51, comprising:
extrapolating said projection data for selected elements of said detector array.

55. A method as recited in claim 51, comprising:
scanning an x-ray beam from said x-ray source over a subject having a portion with a substantially constant field of view at a helical pitch of a non-integral multiple of a slice thickness of said portion.

56. A method as recited in claim 51, comprising:
obtaining projection data of a subject over a reconstruction angle greater than 360°;
performing backprojection using said projection data over said reconstruction angle for a single image; and
weighting said backprojection data based upon a reconstruction angle.

57. A method as recited in claim 51, comprising:
scanning a subject using first and second x-ray beams from an x-ray source having an overlapping area;
backprojecting said projection data to produce backprojection data; and
weighting one of said projection data and said backprojection data based upon a position of a voxel of said subject in an axial plane.

58. A method as recited in claim 51, comprising:
scanning a subject using first and second x-ray beams from said x-ray source having an overlapping area;
backprojecting said projection data to produce backprojection data; and
weighting one of said projection data and said backprojection data of voxels within a same axial plane with a same weight.

59. A method as recited in claim 51, wherein said step of interpolating said projection data comprises:
determining a position where an x-ray path is incident upon said detector array;
interpolating projection data for said x-ray path using a plurality of detector elements proximate to said position from said at least two rows.

60. A method as recited in claim 51, wherein said step of interpolating said projection data comprises:
determining respective distances from said position to a predetermined point in each of said plurality of detector elements proximate to said position; and
interpolating said projection data for said x-ray path based upon said distances.

61. A method as recited in claim 60, wherein determining said respective distances comprises:
determining first distances from said position to said predetermined point for two first detectors elements in a first row in which said point is located; and
determining second distances from said position to said predetermined point for two second detectors in a second row adjacent to said first row.

62. A method as recited in claim 61, comprising:
determining M distances from said position to said predetermined point for 2M detectors in M rows adjacent to said second row, where M is an integer greater than 0.

63. A method as recited in claim 61, wherein said first and second distances are determined using:

$$\text{Back}(I) = \frac{Z(m)}{Z(m+1) + Z(m)} \left[ \frac{L(n+1)}{L(n+1) + L(n)} D(n,m+1) + \frac{L(n)}{L(n+1) + L(n)} D(n+1,m+1) \right] +$$

$$\frac{Z(m+1)}{Z(m+1) + Z(m)} \left[ \frac{L(n+1)}{L(n+1) + L(n)} D(n,m) + \right.$$

-continued $$\frac{L(n)}{L(n+1)+L(n)} D(n,m)\Bigg]$$

where Z(m) and Z(m+1) are detector channel direction distances of said point to said predetermined positions for detector elements in mth and (m+1)th row, and L(n) and L(n+1) are detector row direction distances from said point to said predetermined positions for detector elements in channel n and n+1.

64. A computed tomography system for producing an image of a subject having a portion with a field of view of substantially a given size, comprising:
 a rotating member;
 an x-ray source mounted on said rotating member;
 an x-ray detector mounted on said rotating member; and
 means for helically rotating said rotating member at a pitch that is a non-integral multiple of a slice thickness of said image over said portion.

65. A computed tomography system for producing an image of a subject having a portion with a field of view of substantially a given size, comprising:
 a rotating member;
 an x-ray source mounted on said rotating member;
 an x-ray detector mounted on said rotating member; and
 means for attenuating changeover artifacts using a rotating pitch of said rotating member that is a non-integral multiple of a slice thickness of said image over said portion.

66. A method of operating a computed tomography system having an x-ray source and a detector with a plurality of detector elements, comprising:
 scanning first and second x-ray beams having an overlapping region over a subject; and
 backprojecting using both of said first and second x-ray beams for a first portion of said subject in said overlapping region; and
 backprojecting using one of said first and second x-ray beams for respective second portions of said subject outside of said overlapping region;
 wherein backprojection using both of said first and second x-ray beams comprises:
  determining a first backprojection for a voxel of said first portion using said first x-ray beam;
  determining a second backprojection for said voxel of said first portion using said second x-ray beam; and
  weighting said first and second backprojections; and
 wherein weighting said first and second backprojections comprises:
  determining an intersection point of said first and second x-ray beams;
  determining a position of said voxel; and
  weighting said first and second backprojections based upon a distance in a predetermined direction between said intersection point and said position.

67. A method as recited in claim 66, comprising:
 obtaining first and second projection data associated with said first and second x-ray beams, respectively;
 weighting said first and second projection data; and
 backprojecting for said overlapping region using weighted first projection data and weighted second projection data.

68. A method of operating a computed tomographic system having an x-ray source, comprising:
 scanning a subject using first and second x-ray beams from said x-ray source having an overlapping area;
 obtaining projection data of said subject;
 backprojecting said projection data to produce back-projection data;
 weighting one of said projection data and said backprojection data based upon a position of a voxel of said subject in an axial plane;
 applying constant weighting to voxels located outside of said overlapping area; and
 applying variable weighting to voxels in said overlapping area.

69. A method of operating a computed tomography system having an x-ray source and a detector with a plurality of detector elements arranged in rows, comprising:
 obtaining projection data; and
 extrapolating said projection data for regions of an element proximate to at least one of said uppermost and lowermost edges of said detector;
 wherein extrapolating said projection data comprises:
  determining an intersection point where an x-ray path intersects said element; and
  extrapolating said projection data if said intersection point is located in a predetermined relationship with a predetermined location in said element.

70. A method as recited in claim 69, wherein said predetermined location is an approximate center of said detector element, and extrapolating said projection data comprises at least one of:
 extrapolating said projection data if said intersection point is above an approximate center of a detector element in an uppermost row of said detector; and
 extrapolating said projection data if said intersection point is below an approximate center of a detector element in a lowermost row of said detector.

71. A method as recited in claim 70, wherein extrapolating said projection data comprises:

$$\text{Back}(I) = \frac{Z(N)}{Z(N-1) - Z(N)} \Bigg[ \frac{L(n+1)}{L(n+1)+L(n)} D(n,2) +$$

$$\frac{L(n)}{L(n+1)+L(n)} D(n+1,2) \Bigg] +$$

$$\frac{Z(N-1)}{Z(N-1)+Z(N)} \Bigg[ \frac{L(n+1)}{L(n+1)+L(n)} D(n,1) +$$

$$\frac{L(n)}{L(n+1)+L(n)} D(n,1) \Bigg]$$

where Z(1) and Z(2) are row-direction distances between said intersection point and approximate centers of detector elements in row m and m+1, and L(n) and L(n+1) are channel-direction distances between said intersection point and approximate centers of detector elements in channels n and n+1.

72. A method of operating a computed tomography system having an x-ray source and a detector with a plurality of detector elements arranged in rows, comprising:
 obtaining projection data;
 extrapolating said projection data for regions of an element proximate to at least one of said uppermost and lowermost edges of said detector; and
 extrapolating said projection data from detector elements located in at least one of an uppermost row and a lowermost row and N rows adjacent to said uppermost and lowermost rows in said detector, respectively, where N is an integer greater than 0.

73. A method of operating a computed tomography system having an x-ray source and a detector with a plurality of detector elements arranged in rows, comprising:

obtaining projection data; and extrapolating said projection data for regions of an element proximate to at least one of said uppermost and lowermost edges of said detector;

wherein extrapolating said projection data comprises:

obtaining a row of dummy projection data adjacent to at least one of an uppermost row and a lowermost row of said detector; and extrapolating projection data from at least one of said uppermost row and said row of dummy projection data, and said lowermost row and said row of dummy projection data.

74. A method as recited in claim 73, wherein obtaining said dummy data comprises using projection data from at least one of said uppermost and said lowermost rows.

75. A method as recited in claim 74, wherein said projection data from at least one of said uppermost and lowermost rows is obtained, respectively using:

$D(n,0)=2 \cdot D(n,1)-D(n,2)$ $D(n,N+1)=2 \cdot D(n,N)-D(n,N-1)$ where $D(n,0)$ and $D(n,N+1)$ are dummy data for detector elements in channel n in a dummy row adjacent to said lowermost and uppermost rows, respectively, $D(n,1)$ and $D(n,2)$ are projection data for detector elements in channel n in said lowermost row and a row adjacent to said lowermost row, respectively, and $D(n,N)$ and $D(n,N-1)$ are projection data for detector elements in channel n in said uppermost row and a row adjacent to said uppermost row, respectively.

76. A method as recited in claim 73, wherein extrapolating said projection data comprises interpolating data from at least one of said uppermost and lowermost rows and from an adjacent row of dummy data.

77. A method of operating a computed tomography system having an x-ray source, comprising:

scanning an x-ray beam from said x-ray source over a subject having a portion with a substantially constant field of view at a helical pitch of a non-integral multiple of a slice thickness of said portion.

78. A method of operating a computed tomographic system having an x-ray source, comprising:

at least one of canceling and attenuating changeover artifacts in an image of a subject by setting a helical pitch of rotation of said x-ray source to be a non-integral multiple of a slice thickness of a field of view of said subject.

79. A method of operating a computed tomography system, comprising:

obtaining projection data of a subject over a reconstruction angle greater than 360°;

performing backprojection using said projection data over said reconstruction angle for a single image; and weighting said backprojection data based upon a reconstruction angle;

wherein weighting said backprojection data comprises using a continuous weighting function having a continuous first derivative and having a minimum where said first derivative has a maximum.

80. A method of operating a computed tomography system, comprising:

scanning a subject with first and second x-ray beams having an overlapping area;

obtaining projection data for said subject;

defining a region in said overlapping area;

performing backprojection using projection data from said first and second x-ray beams for said region; and performing back projection for said overlapping area excluding said region using projection data from one of said first and second beams having a smaller cone angle.

81. A method as recited in claim 80, comprising:

obtaining first and second backprojection data for said region using said projection data from said first and second x-ray beams; and weighting said first and second backprojection data.

82. A method of operating a computed tomographic system having an x-ray source, comprising:

scanning a subject using first and second x-ray beams from said x-ray source having an overlapping area;

obtaining projection data of said subject;

backprojecting said projection data to produce backprojection data; and weighting one of said projection data and said backprojection data of voxels within a same axial plane with a same weight.

83. A method as recited in claim 82, comprising:

defining a region in said overlapping area where cone angles of said first and second x-ray beams are substantially equal;

applying constant weighting to voxels located outside of said region; and applying variable weighting to voxels in said region.

* * * * *